US007914559B2

(12) United States Patent
Carls et al.

(10) Patent No.: US 7,914,559 B2
(45) Date of Patent: Mar. 29, 2011

(54) LOCKING DEVICE AND METHOD EMPLOYING A POSTED MEMBER TO CONTROL POSITIONING OF A STABILIZATION MEMBER OF A BONE STABILIZATION SYSTEM

(75) Inventors: Thomas A. Carls, Memphis, TN (US); Eric C. Lange, Collierville, TN (US); Christopher M. Patterson, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1309 days.

(21) Appl. No.: 11/420,890

(22) Filed: May 30, 2006

(65) Prior Publication Data
US 2007/0288002 A1    Dec. 13, 2007

(51) Int. Cl.
*A61B 17/70* (2006.01)
(52) U.S. Cl. .................................................... 606/270
(58) Field of Classification Search ............... 606/264, 606/265, 267, 270
See application file for complete search history.

(56) References Cited

U.S. PATENT DOCUMENTS

| 5,964,760 | A  | 10/1999 | Richelsoph ........................ 606/61 |
| 6,053,917 | A  | 4/2000  | Sherman et al. ................... 606/61 |
| 6,077,262 | A  | 6/2000  | Schläpfer et al. .................. 606/61 |
| 6,139,549 | A  | 10/2000 | Keller ................................ 606/61 |
| 6,296,642 | B1 | 10/2001 | Morrison et al. |
| 6,302,888 | B1 | 10/2001 | Mellinger et al. ................. 606/73 |
| 6,371,957 | B1 | 4/2002  | Amrein et al. .................... 606/61 |
| 6,440,132 | B1 | 8/2002  | Jackson ............................. 606/61 |
| 6,458,132 | B2 | 10/2002 | Choi ................................. 606/61 |
| 6,485,494 | B1 | 11/2002 | Haider ............................. 606/73 |
| 6,565,565 | B1 | 5/2003  | Yuan et al. ........................ 606/61 |
| 6,716,214 | B1 | 4/2004  | Jackson ............................. 606/61 |
| 6,783,527 | B2 | 8/2004  | Drewry et al. .................... 606/61 |
| 6,786,903 | B2 | 9/2004  | Lin ................................... 606/23 |
| 6,793,657 | B2 | 9/2004  | Lee et al. ........................... 606/61 |
| 6,896,677 | B1 | 5/2005  | Lin ................................... 606/61 |
| 6,981,973 | B2 | 1/2006  | McKinley ......................... 606/61 |

(Continued)

FOREIGN PATENT DOCUMENTS
FR    2796545    1/2001
(Continued)

OTHER PUBLICATIONS

International Search Report dated Oct. 26, 2007 relating to corresponding International Application No. PCT/US2007/069456, Applicant: Warsaw Orthopedic, Inc., 3-pages.

(Continued)

*Primary Examiner* — Eduardo C Robert
*Assistant Examiner* — Elana B Fisher

(57) ABSTRACT

A locking device and method are provided for a bone stabilization system which includes a bone anchor, a coupling mechanism and a stabilization member, wherein the coupling mechanism couples the stabilization member to the bone anchor. The locking device includes a seating member and a posted member. The seating member is operatively associated with the coupling mechanism for securing the stabilization member within the coupling mechanism, and is configured with an opening therein. The posted member, which includes an interface member and a post extending therefrom, is configured for disposition between the seating member and the stabilization member with the post extending therefrom being received into the opening in the seating member when the seating member is employed to secure the stabilization member within the coupling mechanism. The post is sized to engage and facilitate control of the stabilization member as the seating member operatively engages the coupling mechanism.

31 Claims, 15 Drawing Sheets

U.S. PATENT DOCUMENTS

| | | | |
|---|---|---|---|
| 7,022,122 B2 | 4/2006 | Amrein et al. | 606/61 |
| 7,625,394 B2 * | 12/2009 | Molz et al. | 606/270 |
| 2001/0047173 A1 | 11/2001 | Schlapfer et al. | |
| 2002/0032443 A1 | 3/2002 | Sherman et al. | 606/61 |
| 2002/0133159 A1 | 9/2002 | Jackson | |
| 2003/0125741 A1 | 7/2003 | Biedermann et al. | 606/61 |
| 2003/0125742 A1 | 7/2003 | Yuan et al. | 606/61 |
| 2003/0167058 A1 | 9/2003 | Shluzas | 606/61 |
| 2004/0030342 A1 | 2/2004 | Trieu et al. | 606/72 |
| 2004/0039383 A1 | 2/2004 | Jackson | 606/61 |
| 2004/0049196 A1 | 3/2004 | Jackson | 606/73 |
| 2004/0053196 A1 | 3/2004 | Mayer et al. | |
| 2004/0158247 A1 | 8/2004 | Sitiso et al. | 606/61 |
| 2004/0172022 A1 | 9/2004 | Landry et al. | 606/61 |
| 2004/0172032 A1 | 9/2004 | Jackson | 606/73 |
| 2004/0186478 A1 | 9/2004 | Jackson | 606/73 |
| 2004/0204711 A1 | 10/2004 | Jackson | 606/61 |
| 2004/0215190 A1 | 10/2004 | Nguyen et al. | 606/61 |
| 2004/0236330 A1 | 11/2004 | Purcell et al. | 606/61 |
| 2004/0243129 A1 | 12/2004 | Moumene et al. | 606/73 |
| 2004/0260283 A1 | 12/2004 | Wu et al. | 606/61 |
| 2005/0021031 A1 | 1/2005 | Foley et al. | 606/61 |
| 2005/0043735 A1 | 2/2005 | Ahmad | 606/73 |
| 2005/0049588 A1 | 3/2005 | Jackson | 606/61 |
| 2005/0049589 A1 | 3/2005 | Jackson | 606/61 |
| 2005/0085813 A1 | 4/2005 | Spitler | 606/61 |
| 2005/0113927 A1 | 5/2005 | Malek | 623/17.16 |
| 2005/0131410 A1 | 6/2005 | Lin | 606/61 |
| 2005/0187548 A1 | 8/2005 | Butler et al. | 606/61 |
| 2005/0187549 A1 | 8/2005 | Jackson | 606/61 |
| 2005/0187555 A1 | 8/2005 | Biedermann et al. | 606/72 |
| 2005/0192570 A1 | 9/2005 | Jackson | 606/61 |
| 2005/0203516 A1 | 9/2005 | Biedermann et al. | 606/61 |
| 2005/0228379 A1 | 10/2005 | Jackson | 606/61 |
| 2005/0228388 A1 | 10/2005 | Brodke et al. | 606/73 |
| 2005/0240180 A1 | 10/2005 | Vienney et al. | 606/61 |
| 2005/0261678 A1 | 11/2005 | Truckai et al. | 606/61 |
| 2005/0261687 A1 | 11/2005 | Garamszegi et al. | |
| 2005/0277924 A1 | 12/2005 | Roychowdhury | 606/61 |
| 2005/0277927 A1 | 12/2005 | Guenther et al. | 606/61 |
| 2005/0277928 A1 | 12/2005 | Boschert | 606/61 |
| 2005/0283157 A1 | 12/2005 | Coates et al. | 606/73 |
| 2006/0025767 A1 | 2/2006 | Khalili | 606/61 |
| 2006/0025771 A1 | 2/2006 | Jackson | 606/61 |
| 2006/0036242 A1 | 2/2006 | Nilsson et al. | 606/61 |
| 2006/0058794 A1 | 3/2006 | Jackson | 606/61 |
| 2006/0064089 A1 | 3/2006 | Jackson | 606/61 |
| 2006/0074418 A1 | 4/2006 | Jackson | 606/61 |

FOREIGN PATENT DOCUMENTS

| | | |
|---|---|---|
| WO | WO 96/06576 A1 | 3/1996 |
| WO | 9702786 | 1/1997 |
| WO | WO 97/14366 A1 | 4/1997 |
| WO | 9832386 | 7/1998 |
| WO | 0197701 | 12/2001 |
| WO | 2005102195 | 11/2005 |

OTHER PUBLICATIONS

International Search Report dated Sep. 20, 2007 relating to corresponding International Application No. PCT/US2007/067492, Applicant: Warsaw Orthopedic, Inc., 4-pages.

International Search Report dated Jan. 21, 2008 relating to corresponding International Application No. PCT/US2007/067455, Applicant: Warsaw Orthopedic, Inc., 6-pages.

"Force Limiting Coupling Assemblies for Spinal Implants", Justis et al., U.S. Appl. No. 11/112,221, filed Apr. 22, 2005.

"Coupling Assemblies for Spinal Implants", Justis et al., U.S. Appl. No. 11/197,799, filed Aug. 5, 2005.

"Bone Anchor System Utilizing a Molded Coupling Member for Coupling a Bone Anchor to a Stabilization Member and Method Therefor", Dewey et al., U.S. Appl. No. 11/414,878, filed May 1, 2006.

"Locking Device and Method, for use in a Bone Stabilization System, Employing a Set Screw Member and Deformable Saddle Member", J. Moore, U.S. Appl. No. 11/414,879, filed May 1, 2006.

* cited by examiner

LOCKING DEVICE AND METHOD EMPLOYING A POSTED MEMBER TO CONTROL POSITIONING OF A STABILIZATION MEMBER OF A BONE STABILIZATION SYSTEM

CROSS-REFERENCE TO RELATED APPLICATIONS

This application contains subject matter which is related to the subject matter of the following applications, which are hereby incorporated herein by reference in their entirety:
"Multi-Axial Bone Attachment Assembly", Coates et al., U.S. Ser. No. 10/870,011, filed Jun. 17, 2004, and published on Dec. 22, 2005 as Patent Application Publication No. US 2005/0283157 A1;
"Coupling Assemblies for Spinal Implants", Justis et al., U.S. Ser. No. 11/197,799, filed Jan. 31, 2006;
"Force Limiting Coupling Assemblies for Spinal Implants", Justis et al., U.S. Ser. No. 11/112,221, filed Jan. 31, 2006;
"Bone Anchor System Utilizing a Molded Coupling Member for Coupling a Bone Anchor to a Stabilization Member and Method Therefor", Dewey et al., U.S. Ser. No. 11/414,878, filed May 1, 2006;
"Locking Device and Method, for Use in a Bone Stabilization System, Employing a Set Screw Member and Deformable Saddle Member", Jeffrey Moore, U.S. Ser. No. 11/414,879, filed May 1, 2006; and
"Locking Device and Method, for Use in a Bone Stabilization System, Employing a Break-Away Interface Member Rigidly Coupled to Seating Member," Dewey et al., U.S. Ser. No. 11/420,911, co-filed herewith.

TECHNICAL FIELD

The present invention relates generally to orthopaedic implants used for the correction of spinal injuries or deformities, and more specifically, but not exclusively, concerns apparatuses and methods for fixing a particular segment or level of the spine, to allow for deformity correction or healing thereof.

BACKGROUND OF THE INVENTION

In the field of spinal surgery, it is known to place implants into vertebrae for a number of reasons, including: (a) correcting an abnormal curvature of the spine; (b) to maintain appropriate vertebral spacing and provide support for broken or otherwise injured vertebrae; and (c) to perform other treatments in the spinal column.

Typical spinal implant or bone stabilization systems utilize a rod as the support and stabilizing element. In such a system, a series of two or more bone fasteners are inserted into two or more vertebrae to be instrumented. A rod or other stabilizing device is then placed within or attached to the head(s) of the bone fastener(s), or is placed within a coupling device that links the rod and the head(s) of the bone fastener(s). The connections between these multiple components are then secured, thereby fixing the supporting construct to multiple levels in the spinal column.

To advance the state of orthopaedic implants, enhancement to such bone stabilization systems are believed desirable, and are addressed herein.

SUMMARY OF THE INVENTION

Briefly summarized, the present invention comprises in one aspect a locking device for use in a bone stabilization system. The bone stabilization system includes a bone anchor, a coupling mechanism and a stabilization member. The coupling mechanism is configured to couple the stabilization member to the bone anchor. The locking device includes a seating member and a posted member. The seating member is operatively associated with the coupling mechanism for securing the stabilization member within the coupling mechanism, and is configured with at least one opening therein. The posted member includes an interface member and at least one post extending therefrom. The posted member is configured for disposition between the seating member and the stabilization member with the at least one post extending from the interface member being received into the at least one opening of the seating member when the seating member is employed to secure the stabilization member within the coupling mechanism. Further, the at least one post is sized to facilitate control of the stabilization member as the seating member operatively engages the coupling mechanism to secure the stabilization member within the coupling mechanism with the posted member disposed between the seating member and the stabilization member.

In another aspect, a bone stabilization system is provided which includes a bone anchor, a stabilization member and a coupling mechanism. The coupling mechanism is configured to operatively connect the bone anchor and the stabilization member. The bone stabilization system further includes a locking device which operatively connects to the coupling mechanism to secure the stabilization member within the coupling mechanism. The locking device includes a seating member and a posted member. The seating member is operatively associated with the coupling mechanism for securing the stabilization member within the coupling mechanism, and is configured with at least one opening therein. The posted member includes an interface member and at least one post extending therefrom. The posted member is configured for disposition between the seating member and the stabilization member with the at least one post extending from the interface member being received into the at least one opening of the seating member when the seating member is employed to secure the stabilization member within the coupling mechanism. Advantageously, the at least one post is sized to facilitate control of the stabilization member as the seating member operatively engages the coupling mechanism to secure the stabilization member within the coupling mechanism with the posted member disposed between the seating member and the stabilization member.

In yet another aspect, a surgical drive tool is presented for inserting/extracting a locking device of a bone stabilization system. The bone stabilization system includes a bone anchor, a coupling mechanism, and a stabilization member, wherein the coupling mechanism is configured to couple the stabilization member to the bone anchor. The locking device includes a seating member operatively associated with the coupling mechanism for securing the stabilization member within the coupling mechanism. The seating member is configured with at least one opening therein. The locking device further includes a posted member, which includes an interface member and at least one post extending therefrom. The posted member is configured for disposition between the seating member and the stabilization member with the at least one post extending from the interface member being received into the at least one opening of the seating member when the seating member is employed to secure the stabilization member within the coupling mechanism.

The surgical drive tool comprises a first component and a second component. The first component is configured to operatively engage the seating member to facilitate positioning of the seating member within the coupling mechanism, while the second component is configured to operatively engage the at least one post of the posted member to facilitate maintaining the posted member fixed and in physical contact with the stabilization member as the first component is employed to secure the seating member within the coupling mechanism, and thereby secure the stabilization member within the coupling mechanism between the posted member and the coupling mechanism.

In a further aspect, a method for stabilizing a spinal column is presented. This method includes: providing a bone stabilization system comprising a bone anchor, a stabilization member, a coupling mechanism, and a locking device, wherein the coupling mechanism is configured to couple the stabilization member to the bone anchor, and the locking device is operatively associated with the coupling mechanism, and wherein the locking device further comprises a seating member configured to threadably engage the coupling mechanism and a posted member configured to control the stabilization member as the seating member threadably engages the coupling mechanism, the posted member comprising an interface member and at least one post extending therefrom, and wherein the seating member includes at least one opening therein; positioning the stabilization member in the coupling mechanism; positioning the posted member with the at least one post thereof within the at least one opening of the seating member, and threading the seating member into the coupling mechanism while holding the at least one post of the posted member fixed and in physical contact with the stabilization member, thereby maintaining control of the stabilization member as the seating member engages the coupling mechanism; and continuing to threadably advance the seating member into the coupling mechanism, thereby causing the posted member to become fixed between the seating member and the stabilization member, and securing the stabilization member between the posted member and the coupling mechanism.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

BEST MODE FOR CARRYING OUT THE INVENTION

Generally stated, presented herein is an enhanced locking device for a bone stabilization or anchor system, as well as surgical drive tools for inserting/extracting the locking device and surgical methods for stabilizing a column employing a bone stabilization system and the enhanced locking device. The bone stabilization system includes a bone anchor (e.g., a screw), a coupling mechanism (e.g., an integral head) and a stabilization member (e.g., a rod), wherein the coupling mechanism is configured to couple the stabilization member to the bone anchor. The enhanced locking device includes a seating member (e.g., a setscrew) and a posted member. The seating member is operatively associated with the coupling mechanism for securing the stabilization member within the coupling mechanism, and includes at least one opening therein. The posted member includes an interface member and at least one post extending therefrom. The posted member is configured for disposition between the seating member and the stabilization member with the at least one post extending from the interface member being received into the at least one opening of the seating member when the seating member is employed to secure the stabilization member within the coupling mechanism. The at least one post is sized to facilitate handling of the separate seating member and posted member pieces, as well as control of the stabilization member as the seating member operatively engages the coupling mechanism to secure the stabilization member within the coupling mechanism with the posted member disposed between the seating member and the stabilization member. Various embodiments of the seating member and posted member, as well as various embodiments of the surgical drive tool are described below with reference to FIGS. 4-15A. One embodiment of a bone stabilization system is first presented, however, with reference to FIGS. 1-3.

Figure 1:
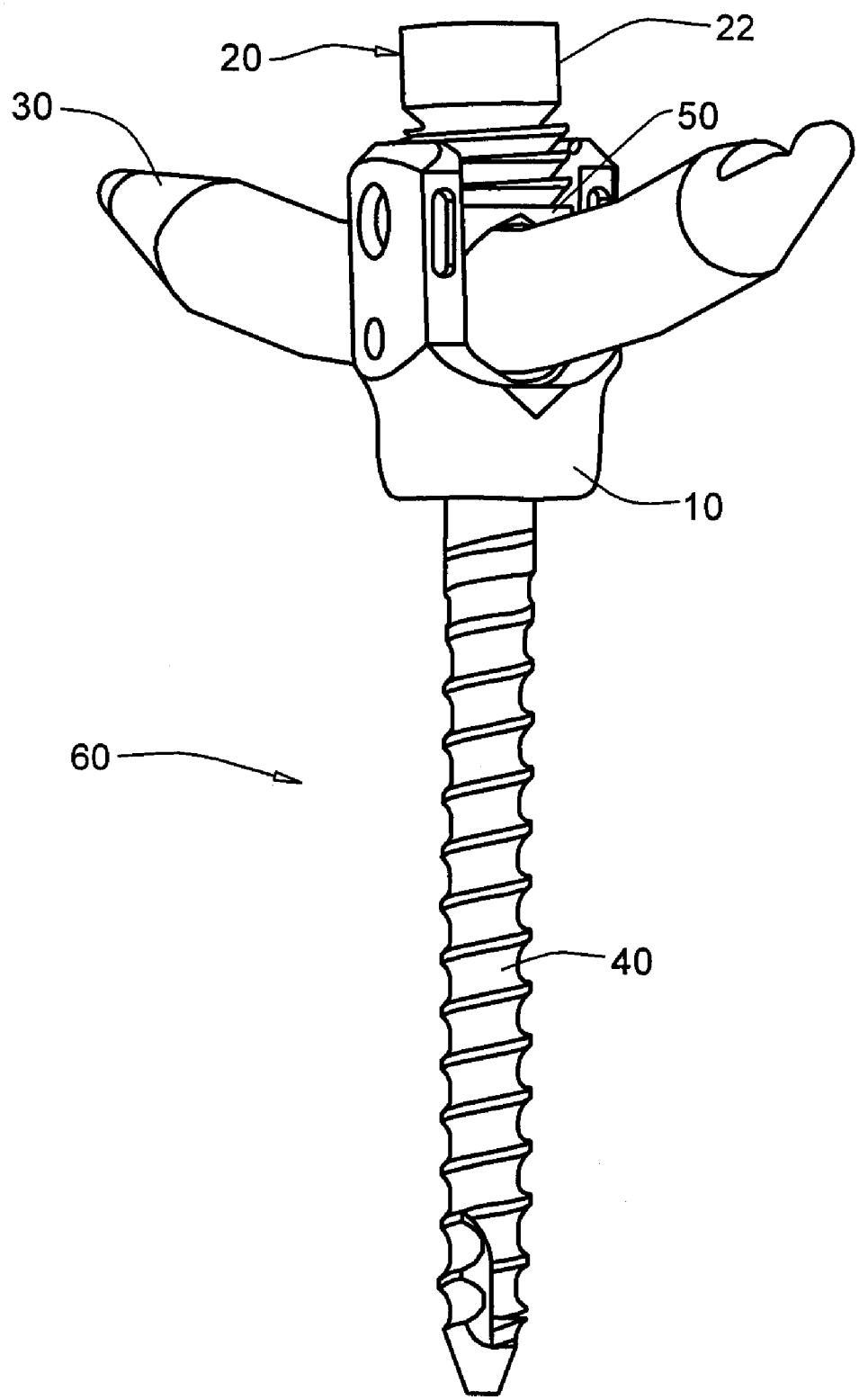
FIG. 1 is a perspective view of one embodiment of a bone stabilization system, in accordance with an aspect of the present invention.

FIG. 1 depicts one embodiment of a bone stabilization system 60, which includes a coupling mechanism 10, a locking device 20, (comprising, in this embodiment, a seating member 22 and a saddle member 50), a stabilization member 30, and a bone anchor 40. When used in a spine to secure multiple levels of the spinal column, each bone anchor 40 is placed within an individual vertebrae, and a coupling mechanism 10 is attached to the implanted bone anchor 40. Following placement of multiple bone anchors and coupling mechanisms, an appropriately dimensioned stabilization member 30, which spans one or more levels of the affected vertebral region, is placed within the coupling mechanisms 10 and secured in place employing multiple locking devices. In this initial embodiment, locking device 20 includes seating member 22 and saddle member 50. When the locking device is in use, stabilization member 30 is frictionally held in place between coupling mechanism 10 and seating member 22 by saddle member 50.

In one implementation, the locking device may be formed with a deformable saddle member 50 to reduce the resultant stresses realized in stabilization member 30 by decreasing the generation of surface stress risers when fixed within coupling mechanism 10 by being fabricated from the same or similar material as stabilization member 30 and having a concave distal interface surface that further deforms to the shape of stabilization member 30.

Figure 2:
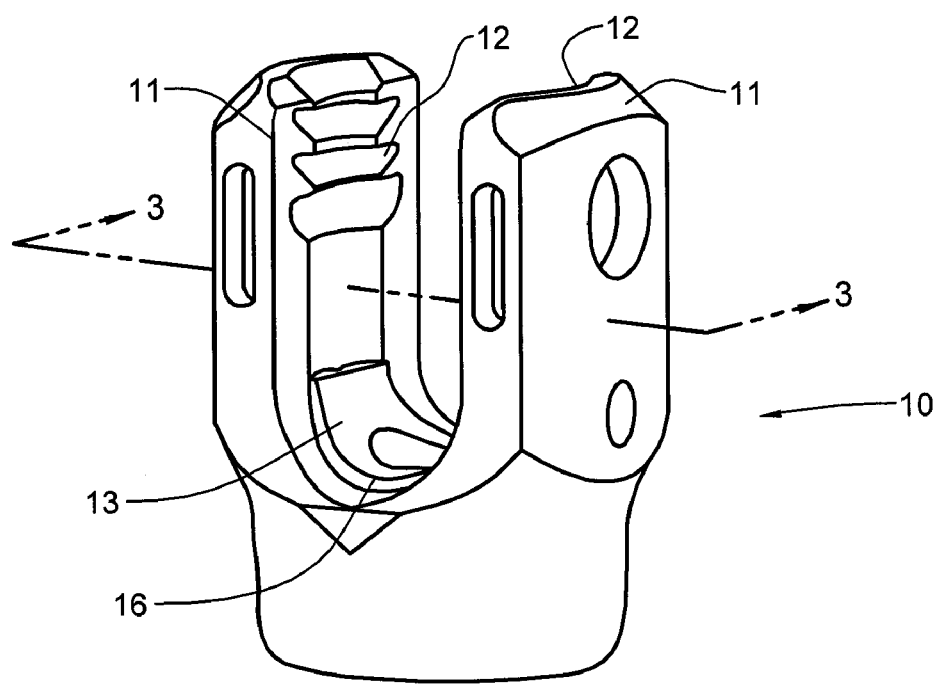
FIG. 2 is a perspective view of one embodiment of a coupling mechanism, in accordance with an aspect of the present invention.
Figure 3:
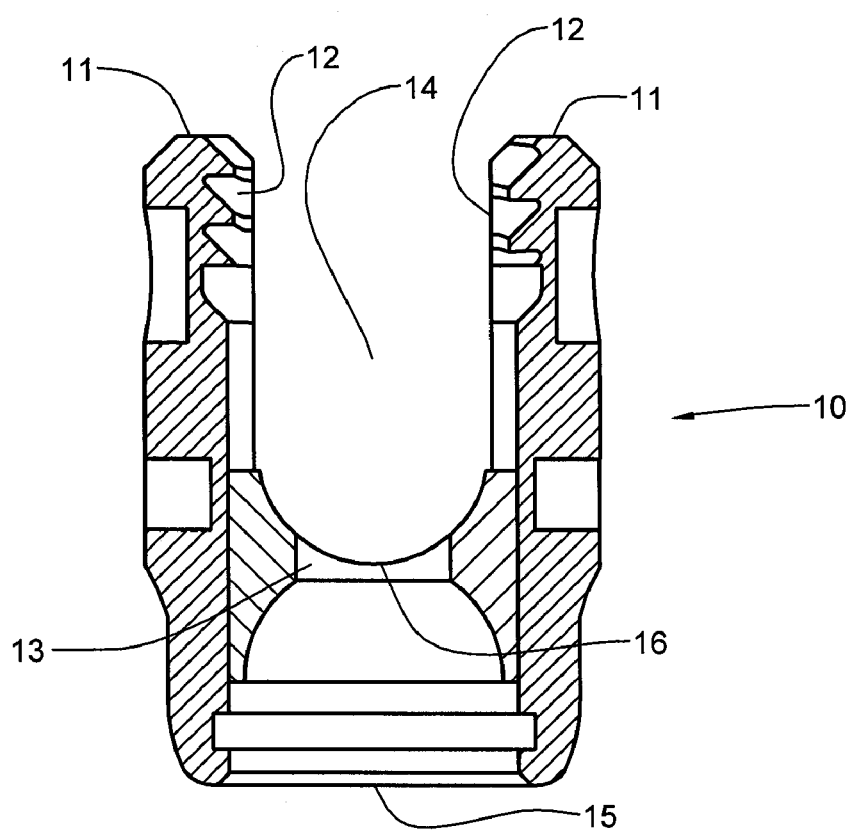
FIG. 3 is a cross-sectional elevational view of the coupling mechanism of FIG. 2, taken along line 3-3, in accordance with an aspect of the present invention.

With further reference to FIGS. 2 and 3, coupling mechanism 10 of bone stabilization system 60 includes a channel 14 defined by a seat 13 and a pair of coupling arms 11. Coupling arms 11, which are disposed parallel and project in an upward manner from seat 13, together with seat 13 form a U-shaped channel 14, which is appropriately sized to receive stabilization member 30. The internal walls of coupling arms 11 include internal threads 12 or alternatively an internal cam surface (not shown) to engage external threads of seating member 22. Typically, at least one through hole 15 is located directly below seat 13 in coupling mechanism 10. In one approach, a bone anchor is inserted into hole 15 prior to the placement of the stabilization member. The longitudinal axis of the bone anchor may be at a fixed angle relative to coupling mechanism 10 following insertion into hole 15 or be allowed to pivot within hole 15. Hole 15 may be counter bored, counter sunk, slotted, have a spherical seat, keyed or any combination or derivation of these manufacturing techniques, to allow the top portion of the anchor head to sit below the seat floor 16.

In this example, seating member 22 threadably engages with internal threads 12 of coupling mechanism 10, although it should be understood by those skilled in the art that other configurations are possible, including a seating member configured to include an external cam surface (not shown) that engages with an internal cam surface (not shown) located on the internal surface of coupling arms 11. In an unlocked position, stabilization member can move freely within channel 14. When in a locked position, with the locking device substantially engaged with internal threads 12 of the coupling mechanism, pressure or a compressive force is applied across the distal interface surface of the saddle member onto the stabilization member.

Stabilization member 30 (see FIG. 1) is typically shaped as an elongate and continuous orthopaedic implant, for example, in the shape of a rod. Alternative stabilization members may include, but are not limited to plates, bars, tethers, cables, elastic structures and dynamic stabilization members (not shown). Stabilization member 30 may be fabricated from a plastic material, such as a polyetheretherketone (PEEK) polymer. Alternatively, stabilization member 30 may be fabricated from a material comprising carbon fiber composite polymers, bio-compatible metals, shape memory metals, resorbable polymers, bio-inert polymeric materials, thermoplastic polymers, thermoset polymers or any combination of these materials.

As one detailed example, saddle member 50 may be fabricated from a deformable plastic material, such as polyetheretherketone (PEEK) polymer. Alternatively, saddle member 50 may be fabricated from another deformable material selected from the group consisting of carbon fiber composite polymers, UHMWPE, shape memory metals, resorbable polymers, bio-inert polymeric materials, thermoplastic polymers, thermoset polymers and any combinations of these materials. In one implementation, the material used to comprise saddle member 50 will have a flexural modulus that is equivalent or similar to the flexural modulus of stabilization member 30. One possible range of the flexural modulus of saddle member 50 is from about 30 to 115 MPa.

Bone anchor 40 is typically configured as a bone screw, although alternative bone anchors may be utilized including bone fixation posts (not shown), bone staples (not shown), hooks (not shown), and moveable head screws (not shown). It should be understood by those skilled in the art that the bone anchor-coupling mechanism structures described herein are presented by way of example only and that other configurations may be used, including coupling mechanism 10 being configured integrally with bone anchor 40.

Figure 4:
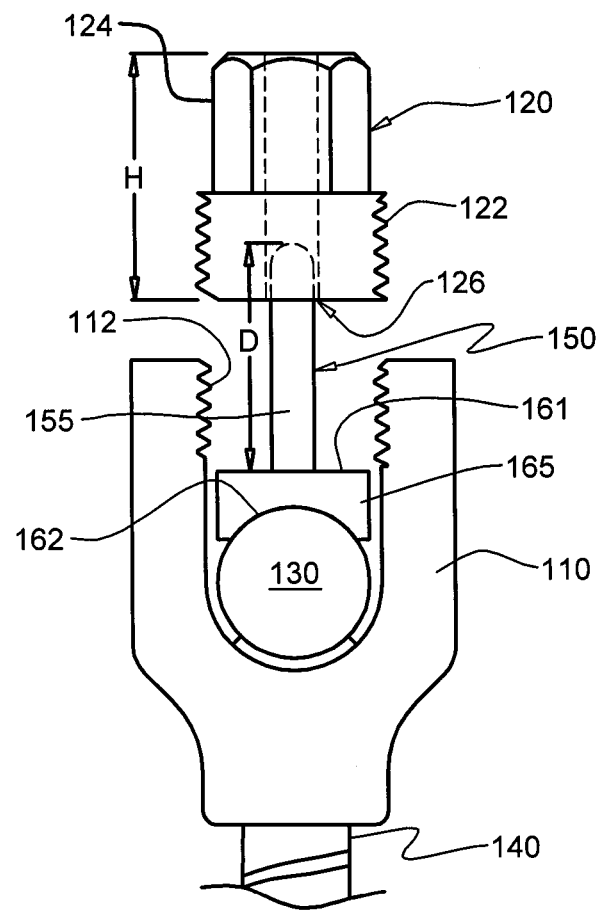
FIG. 4 is a partial elevational view of one embodiment of a bone stabilization system employing a locking device comprising a seating member and a posted member, shown with the posted member in operative position and the seating member exploded from the coupling mechanism, in accordance with an aspect of the present invention.
Figure 4A:
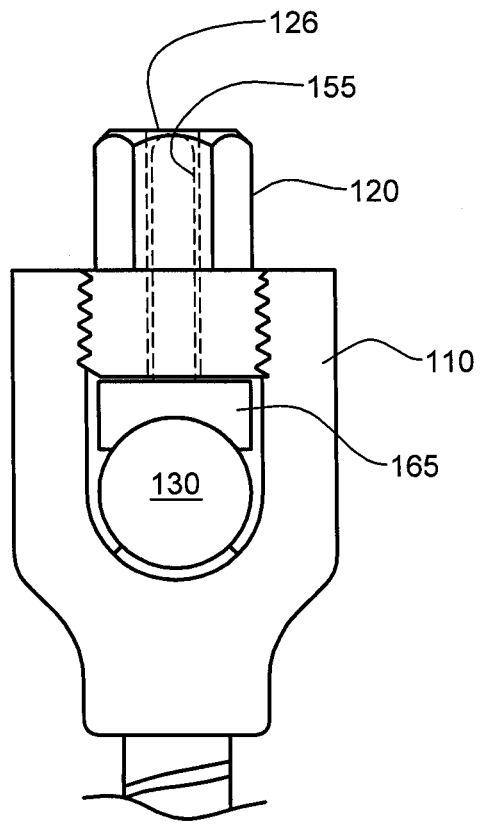
FIG. 4A is a partial elevational view of the bone stabilization system of FIG. 4, showing the seating member operatively engaging the coupling mechanism with the posted member disposed between the seating member and the stabilization member, in accordance with an aspect of the present invention.

FIGS. 4 & 4A depict an alternate embodiment of a bone stabilization system, in accordance with an aspect of the present invention. This embodiment is similar to the bone stabilization system embodiment of FIGS. 1-3; however, saddle member 50 of the initial embodiment is replaced by a posted member 150, and the seating member 20 is replaced by a seating member 120 configured in one embodiment as shown in FIGS. 4 & 4A. More particularly, this bone stabilization system includes a coupling mechanism 110, a locking device (comprising seating member 120 and a separate posted member 150), a stabilization member 130, and a bone anchor 140. When in use, bone anchor 140 is placed within an individual vertebrae, with a coupling mechanism 110 attached thereto. Coupling mechanism 110 is appropriately dimensioned to receive stabilization member 130, which spans one or more levels of the effected vertebral region. In this embodiment, coupling mechanism 110 again includes two upwardly projecting arms which have (by way of example) threads 112 on an inner surface thereof for threadably receiving seating member 120 of the locking device.

As shown, seating member 120 includes a threaded portion 122 and a drive tool receiving portion 124 having, in this example, a hexagonal-shaped perimeter. A central cannulation or opening 126 extends through seating member 120 and is sized to receive a post 155 of posted member 150. Those skilled in the art will understand from the description provided herein that multiple posts 155 may be provided extending from an interface member 165 of the posted member 150, in which case multiple corresponding openings 126 would be provided within seating member 120. Various posted member embodiments are presented below with reference to FIGS. 7A-10C. In the embodiment illustrated in FIGS. 4 & 4A, one central post 155 extends from a proximal surface 161 of interface member 165 and is received within opening 126 of the seating member. The distal surface 162 of interface member 165 is saddle-style contoured to facilitate physical contact with stabilization member 130.

Post 155 is sized to extend from interface member 165 a sufficient distance D to allow a surgical drive instrument to couple thereto to facilitating holding the posted member and the seating member together, as well as to hold the posted member fixed and in physical contact with the stabilization member to facilitate control of the stabilization member as the seating member 120 is operatively engaged with the coupling mechanism 110. Various embodiments of a surgical drive tool are presented below with reference to FIGS. 13-15A.

The distance D that the post extends from the interface member may vary with the implementation, and may even extend a distance greater than the height H of the seating member, as well as be provided with a break-off line to facilitate removal of a break-off portion of the post after seating of the seating member within the coupling mechanism. In the embodiment of FIGS. 4 & 4A, post 155 is shown to extend from interface member 165 a distance equal to the height of seating member 120, as best shown in FIG. 4A, wherein post 155 extends within the central opening 126 of seating member 120.

Figure 5:
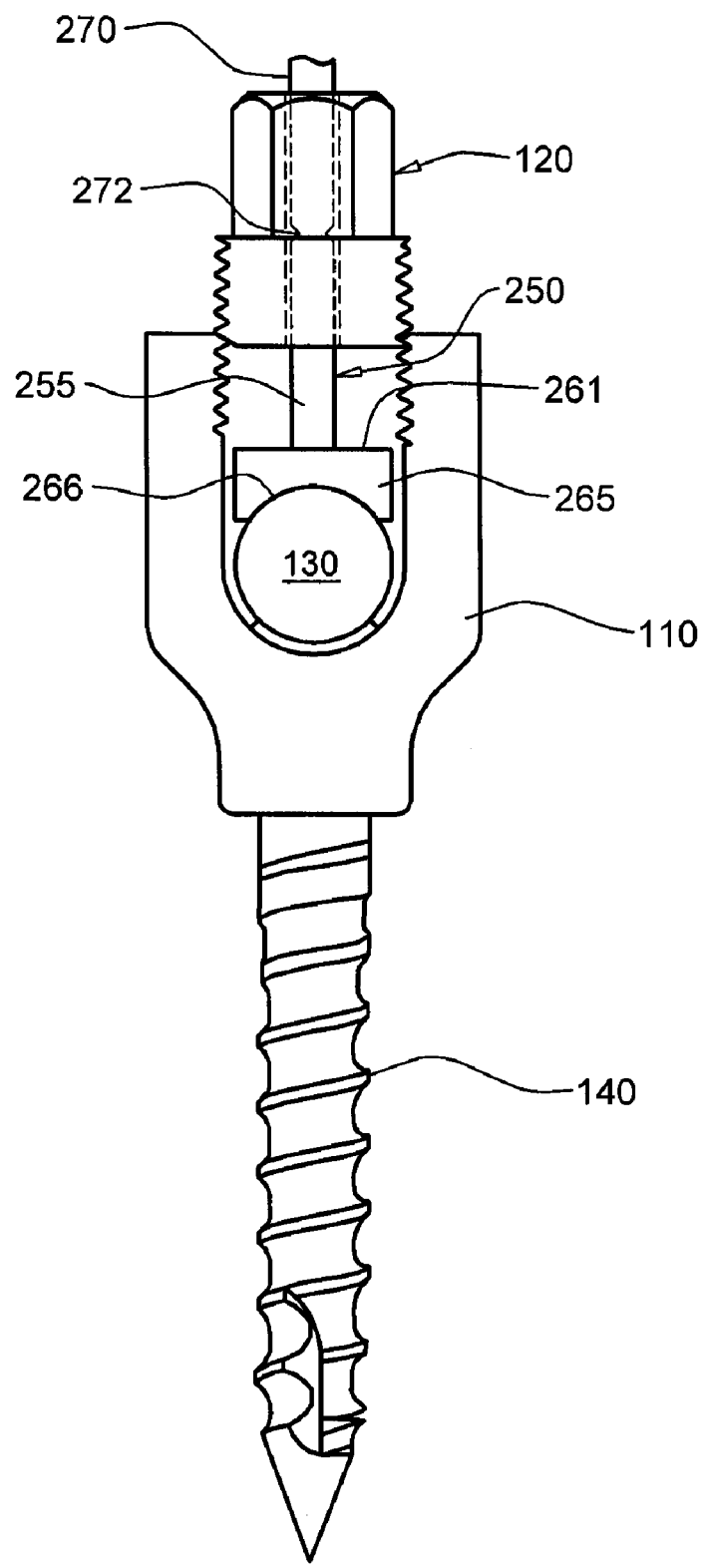
FIG. 5 is an elevational view of a bone stabilization system employing another embodiment of a locking device wherein the seating member is beginning threaded engagement with the coupling mechanism, and the posted member is disposed in operative position between the stabilization member and the seating member, in accordance with an aspect of the present invention.
Figure 5A:
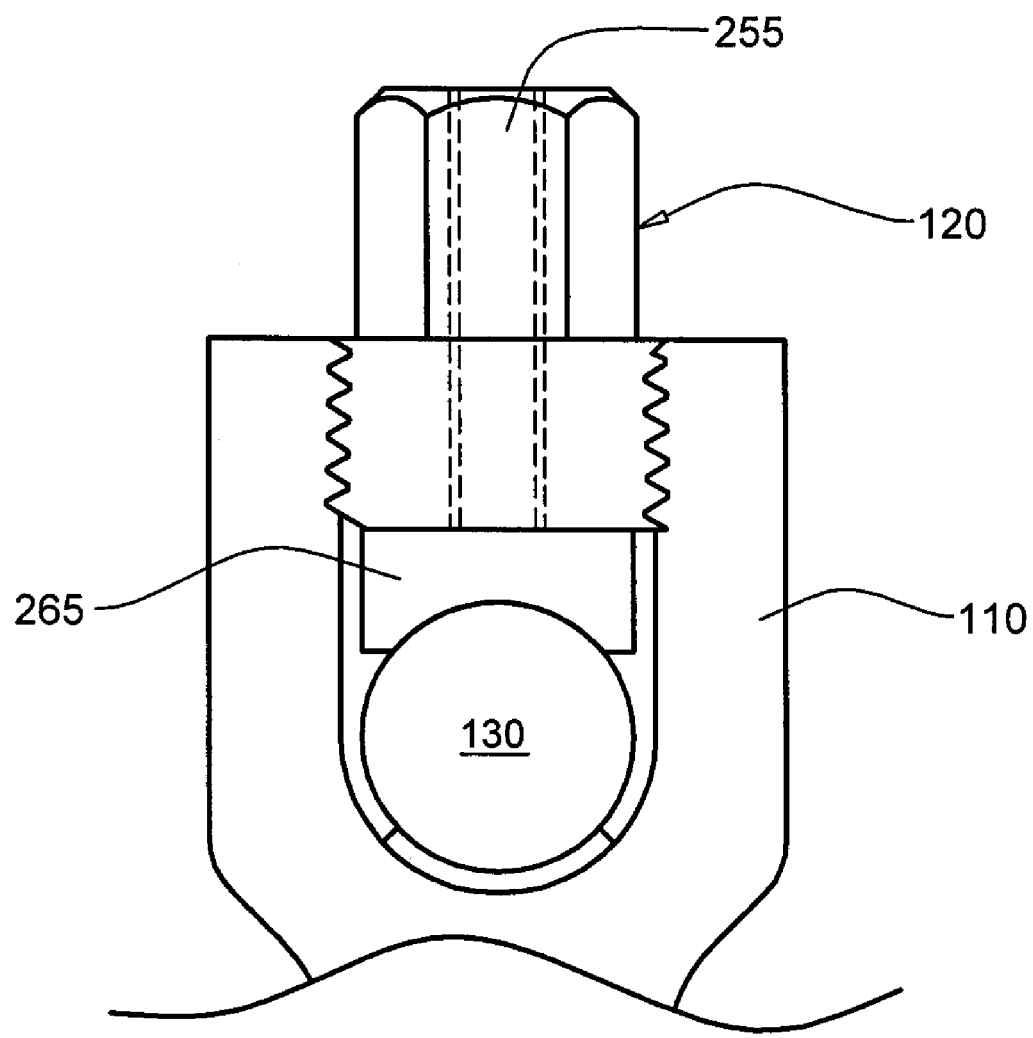
FIG. 5A is a partial elevational view of the bone stabilization system of FIG. 5 after the seating member is fully threadably engaged with the coupling mechanism to secure the stabilization member between the coupling mechanism and the posted member, in accordance with an aspect of the present invention.

FIGS. 5 & 5A depict an alternate embodiment of a locking device for a bone stabilization system, which again includes a bone anchor 140, a stabilization member 130 and a coupling mechanism 110 configured to couple the stabilization member to the bone anchor by cradling the stabilization member as shown. The stabilization member 130 may extend through any number of coupling mechanism/bone anchor assemblies. In this embodiment, the locking device comprises a seating member 120 such as described above in connection with FIGS. 4 & 4A, and an alternate embodiment of a posted member 250. In this alternate embodiment, posted member 250 includes an interface member 265 and a post 255 extending from a proximal surface 261 thereof. The distal surface 266 of interface member 265 is again saddle-style contoured to physically engage a portion of the outer surface of stabilization member 130. Post 255 includes a circumferential break-off line 272 around the perimeter thereof which defines a break-off portion 270. The break-off line 272 is disposed in this embodiment a distance from proximal surface 261 equal to or less than the height of seating member 120. This is illustrated in FIG. 5A wherein post 255 has been broken along break-off line 272 and break-away portion 270 (see FIG. 5) has been removed. The remaining post 255 portion is disposed within the opening provided within the seating member 120.

In operation, a surgical drive tool component engages post 255 as seating member 120 threadably engages coupling mechanism 110 to hold the posted member fixed and in physical contact with stabilization member 130 to maintain the stabilization member in a fixed position during placement of the locking device in operative position with the coupling mechanism. When in operative position, the locking device locks the posted member, and in particular, interface member 265 between seating member 120 and stabilization member 130 to fixate the stabilization member relative to the coupling mechanism.

Figure 6:
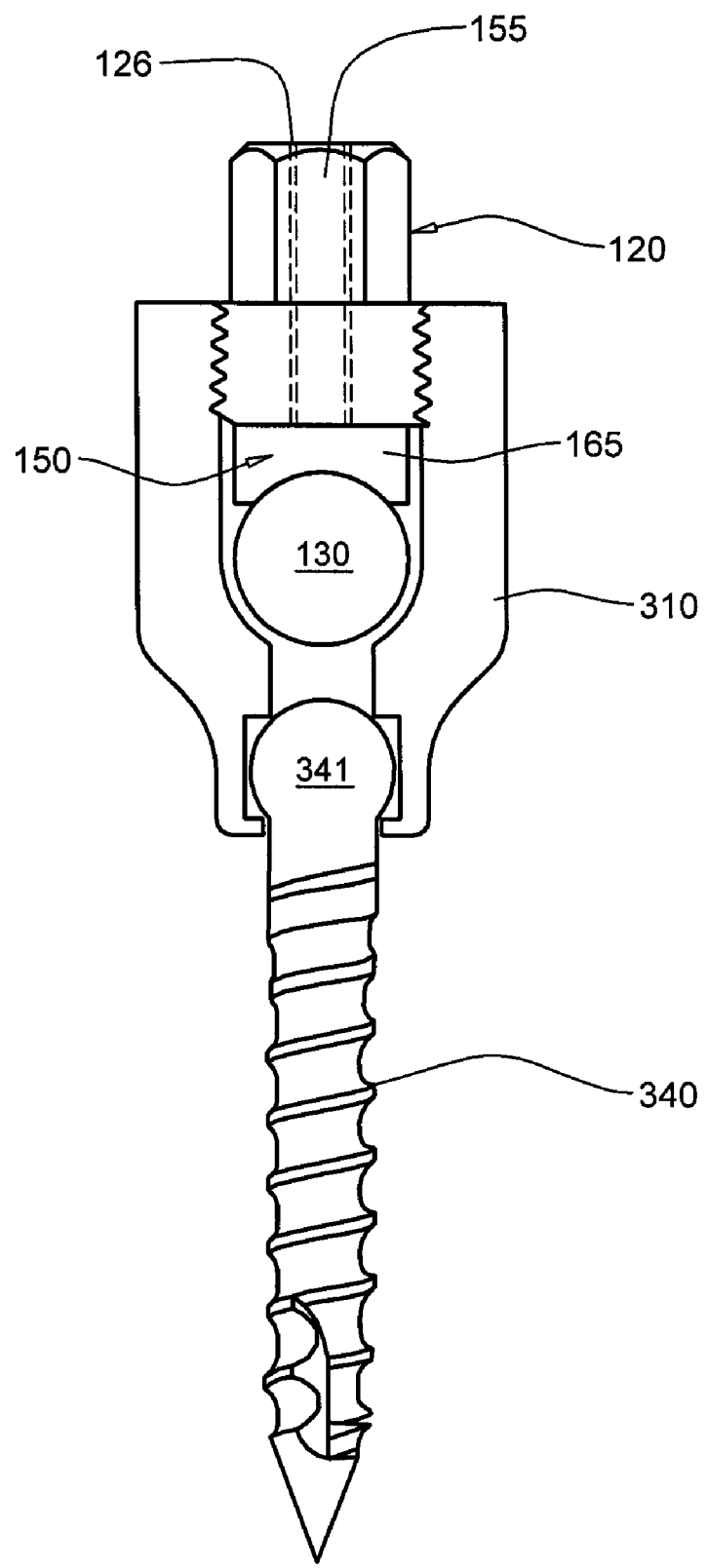
FIG. 6 is an elevational view of an alternate embodiment of a bone stabilization system employing a polyaxial coupling mechanism-to-bone anchor interface, and a locking device such as illustrated above in connection with FIGS. 4-4A, in accordance with an aspect of the present invention.

FIG. 6 depicts an alternate embodiment of a bone stabilization system wherein a bone anchor 340 includes a head 341 which is pivotally engaged by a coupling mechanism 310 such that the coupling mechanism-to-bone anchor interface is polyaxial, which may allow easier positioning of the bone stabilization system relative to patient geometry. The coupling mechanism is again sized to receive a stabilization member 130, and in this embodiment, the locking device is shown operatively positioned with the seating member 120 fully threadably engaged with the coupling mechanism 310. When fully engaged, posted member 150 is positioned between the seating member 120 and the stabilization member 130, with the interface member 165 in physical contact with the stabilization member and the at least one post 155 extending therefrom being received within a corresponding at least one opening 126 in the seating member 120.

Figure 7A:
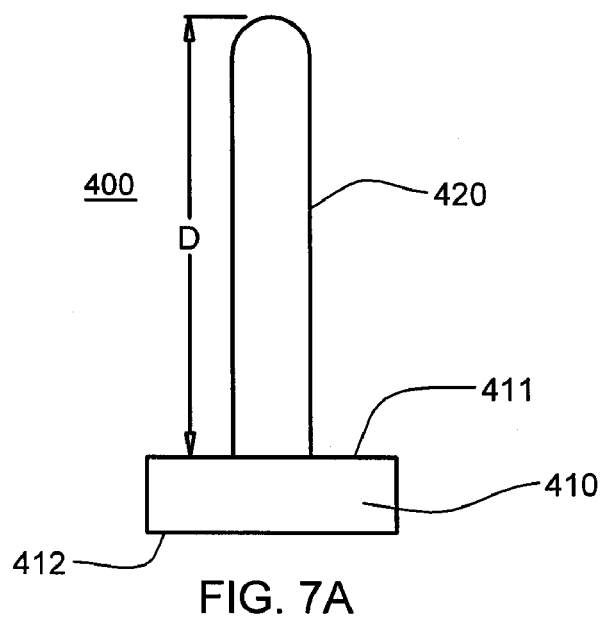
FIG. 7A is an elevational view of one embodiment of a posted member, in accordance with an aspect of the present invention.
Figure 7B:
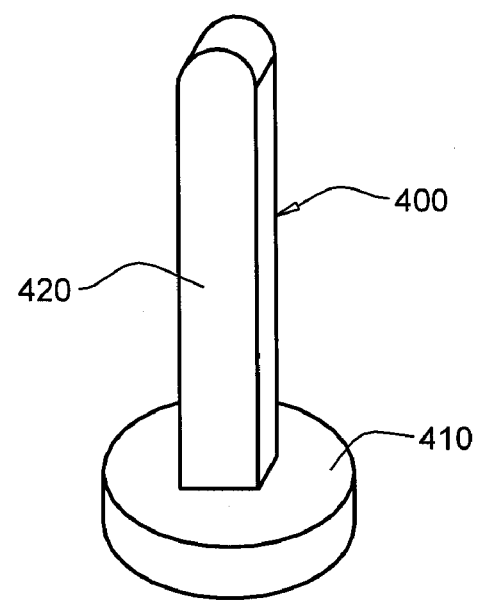
FIG. 7B is an isometric view of the posted member of FIG. 7A, in accordance with an aspect of the present invention.

FIGS. 7A & 7B depict another embodiment of a posted member 400, in accordance with an aspect of the present invention. In this embodiment, posted member 400 again comprises an interface member 410, with at least one post 420 extending a distance D from a proximal surface 411 thereof. The distal surface 412 of interface member 410 is shown to be a planar surface, by way of example. The distance D that the post extends from the proximal surface 411 of interface member 410 is sized to facilitate engagement of a surgical drive tool with the post to facilitate handling of the posted member and seating member together, as well as to facilitate control of the stabilization member as the seating member operatively engages the coupling mechanism to secure the stabilization member within the coupling mechanism with the posted member disposed between the seating member and the stabilization member. The stabilization member can comprise a number of cross-sectional configurations, including circular, oblong, or elliptical, etc. Thus, the posted member facilitates holding the stabilization member in a desired position within the coupling mechanism as the locking device is secured to the coupling mechanism. The distance D can vary, and is in one example at least one-half the height of the seating member. In the embodiments illustrated in FIGS. 4-6, the seating member includes one or more openings extending therethrough which allow the surgical drive tool (see FIGS. 13-15A) to engage the post to hold the post while the seating member is operatively positioned relative to the coupling mechanism.

Figure 7C:
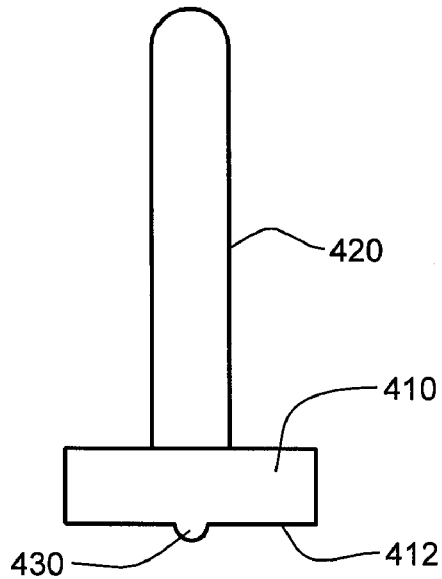
FIG. 7C is an elevational view of an alternate embodiment of a posted member wherein one or more protrusions extend from the distal surface of the posted member, in accordance with an aspect of the present invention.

FIG. 7C depicts the posted member of FIGS. 7A & 7B with the addition of one or more protrusions 430 extending from distal surface 412 of interface member 410. Protrusion(s) 430 may be rounded or pointed and configured to facilitate interfacing of the posted member to the stabilization member. For example, if the stabilization member is manufactured of a biocompatible metal, then protrusions 430 may assist in fixating the stabilization member relative to the posted member.

Figure 8A:
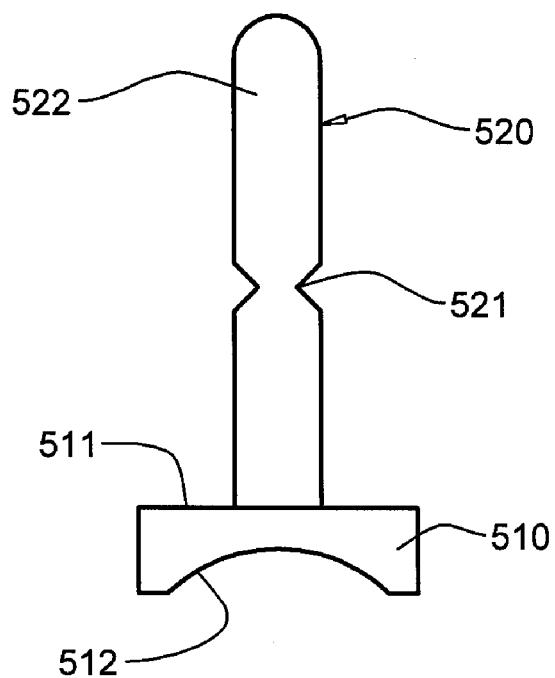
FIG. 8A is an elevational view of another embodiment of a posted member, in accordance with an aspect of the present invention.
Figure 8B:
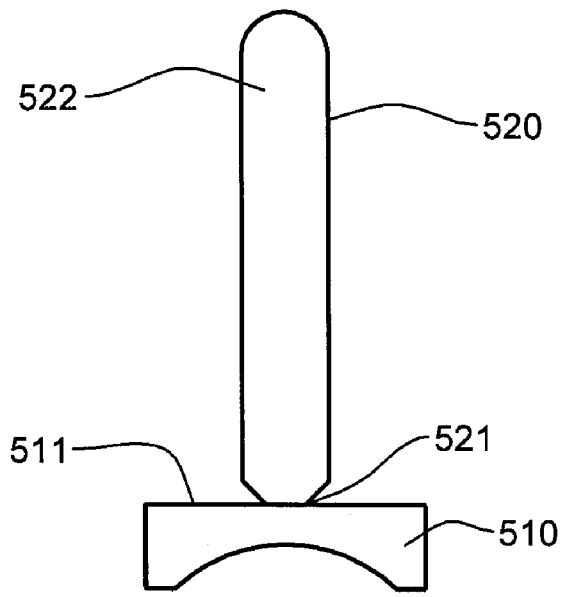
FIG. 8B is an elevational view of still another embodiment of a posted member, in accordance with an aspect of the present invention.

FIGS. 8A & 8B depict alternate embodiments of the posted member, wherein a post 520 again extends from the proximal surface 511 of an interface member 510. In this embodiment, the distal surface 512 of interface member 510 is saddle-style contoured to conform and physically contact to a portion of the stabilization member in a manner similar to the embodiment shown in FIGS. 4-5A. Further, in this embodiment post 520 is configured with a circumferential break-off line 521 disposed around the perimeter of the post. This break-off line can be formed, for example, by circumferentially removing material from post 520 at the desired location. In FIG. 8A, break-off line 521 is shown intermediate the ends thereof, while in FIG. 8B, break-off line 521 is at the interface between post 520 and interface member 510.

In the embodiment of FIG. 8A, after placing the seating member in operative engagement with the coupling mechanism, the surgical drive tool is employed to twist off break-off portion 522 of post 520. The remaining portion of post 520 in FIG. 8A extends from surface 511 a distance into the seating member less than or equal to the height of the seating member, as explained above in connection with the embodiments of FIGS. 4-6. In the embodiment of FIG. 8B, the entire post is the break-off post portion 522, and is removed after placement of the seating member in operative engagement with the coupling mechanism, leaving only interface member 510 between the seating member and the stabilization member. In this implementation, proximal surface 511 of interface member 510 is substantially planar after break-off of the post. Twist off of the break-off post portion along the circumferential break-off line can be designed to occur at a particular torque value applied to the post. Considerations for the determination of this torque value include the type of material employed for the post, the diameter of the post, as well as the amount of material circumferentially removed from the post to define the circumferential break-off line.

Figure 9A:
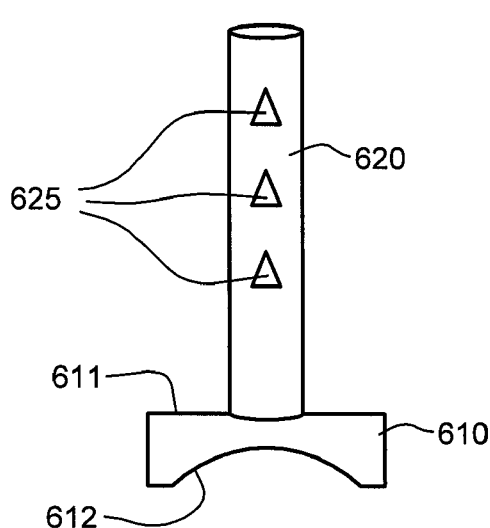
FIG. 9A is an elevational view of a further embodiment of a posted member, in accordance with an aspect of the present invention.
Figure 9B:
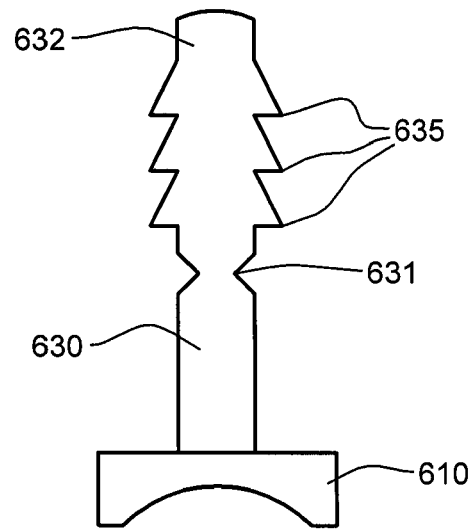
FIG. 9B is an elevational view of another embodiment of a posted member, in accordance with an aspect of the present invention.

FIGS. 9A & 9B depict further variations of the posted member, in accordance with aspects of the present invention. In FIG. 9A, the posted member again includes an interface member 610 and at least one post 620 extending from a proximal surface 611 thereof. The distal surface 612 of interface member 610 is saddle-style contoured to conform to a portion of the stabilization member (not shown). In this embodiment, post 620 includes multiple key slots 625 placed circumferentially about the post to facilitate interfacing of the surgical drive tool (not shown) with the post, and thereby enhance holding of the post in fixed position during operative engagement of the seating member with the coupling mechanism.

FIG. 9B depicts an alternate embodiment of the posted member, wherein a post 630 again extends from interface member 610. In this embodiment, post 630 includes barbs 635 extending radially outward from a break-off post portion 632 thereof defined by a break-off line 631. Barbs 635 are configured to facilitate interfacing of a surgical drive tool to the post during operative engagement of the seating member to the coupling mechanism to hold the posted member in fixed physical contact with the stabilization member, and thereby maintain the stabilization member in fixed position within the coupling mechanism. Additionally, barbs 635 facilitate retention of break-off post portion 632 within the surgical drive tool after twist-off of the break-off post portion from the remaining portion of the posted member.

Figure 10A:
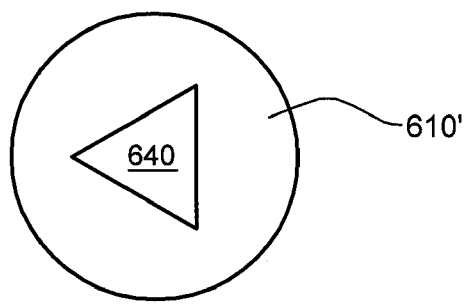
FIG. 10A is a top plan view of yet another embodiment of a posted member, in accordance with an aspect of the present invention.
Figure 10B:
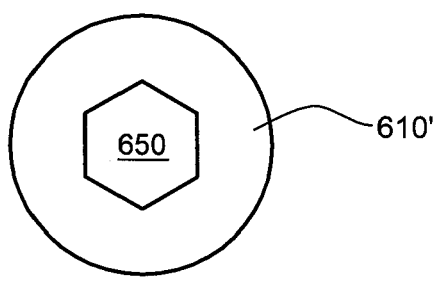
FIG. 10B is a top plan view of a further embodiment of a posted member, in accordance with an aspect of the present invention.
Figure 10C:
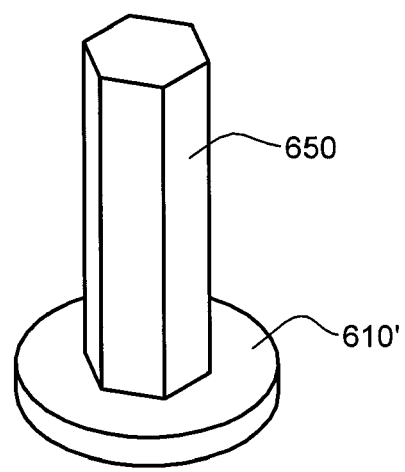
FIG. 10C is an isometric view of the posted member of FIG. 10B, in accordance with an aspect of the present invention.

FIGS. 10A and 10B & 10C depict further geometric post variations for the posted member. In the top plan view of FIG. 10A, the posted member is shown to comprise an interface member 610' from which a triangular post 640 projects. In this example, post 640 is again an elongate post extending from interface member 610' in a manner similar to the posts described above. However, in this embodiment, post 640 has a triangular transverse cross-section as shown in the plan view. Any desired geometric configuration can be employed for the post. FIGS. 10B & 10C depict an alternate embodiment wherein a hexagonal-shaped post 650 extends from interface member 610'. Other transverse cross-sections for the post could include circular, rectangular, oblong, etc.

Figure 11:
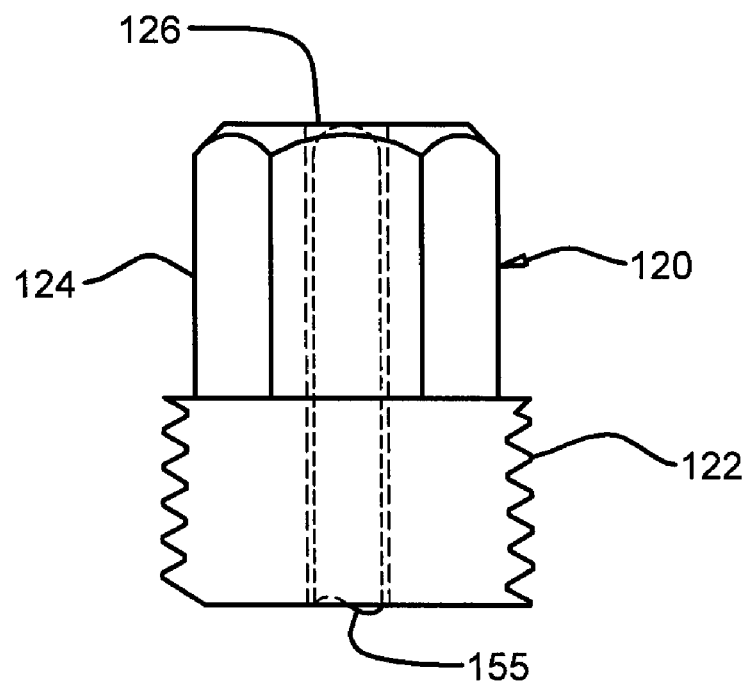
FIG. 11 is an elevational view of one embodiment of a seating member, with a partial post of a posted member disposed therein, in accordance with an aspect of the present invention.
Figure 12A:
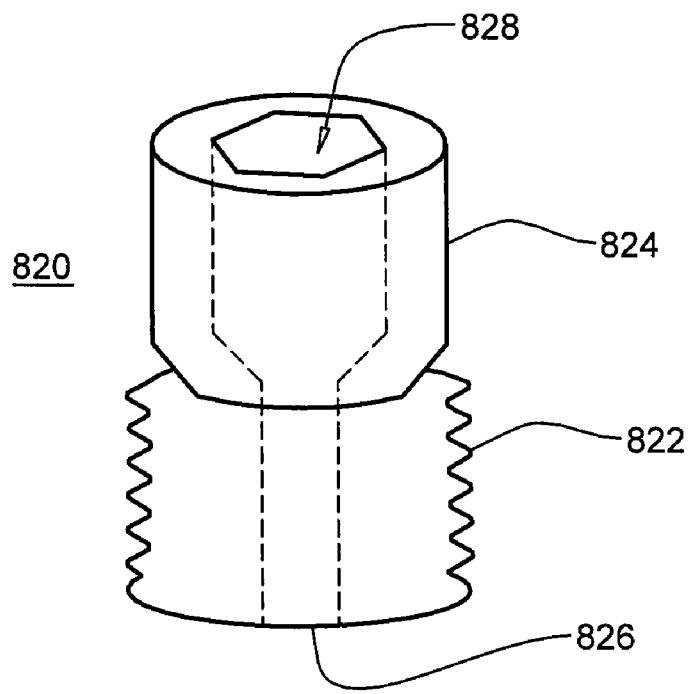
FIG. 12A is an isometric view of another embodiment of a seating member, in accordance with an aspect of the present invention.
Figure 12B:
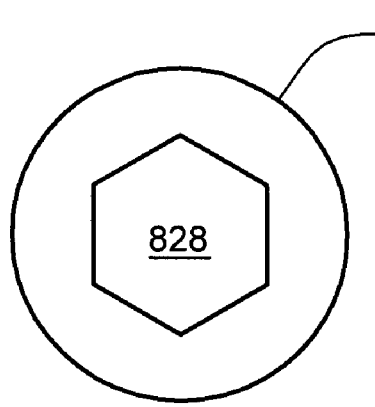
FIG. 12B is a top plan view of the seating member of FIG. 12A, in accordance with an aspect of the present invention.
Figure 12C:
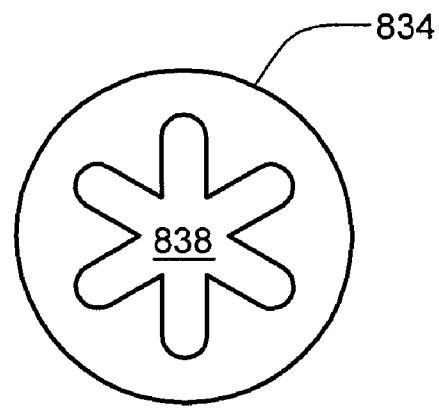
FIG. 12C is a top plan view of a further embodiment of a seating member, in accordance with an aspect of the present invention.

FIGS. 11-12C present various embodiments of a seating member to be employed in a locking device, in accordance with aspects of the present invention. FIG. 11 again repeats seating member 120 from FIGS. 4-6. A partial depiction of post 155 is shown to extend within center opening 126 of seating member 120. In one implementation, center opening 126 extends through seating member 120. Seating member 120 further includes a threaded portion 122 and a drive tool receiving portion 124, which in this embodiment has a hexagonal-shaped outer perimeter to be engaged by a corresponding hexagonal-shaped drive tool (not shown).

Seating member 120 may be fabricated from a titanium alloy, for example, the alloy Ti-6Al-4V. Alternatively, the seating member may be fabricated from one or more of CP titanium, cobalt-chromium, a 300 series stainless steel, carbon fiber materials, carbon fiber composites, resorbable polymers, bio-inert polymeric materials, thermoplastic polymers, thermoset polymers, or any combination of these materials. The posted member may be fabricated of the same material as the seating member, or different material. For example, the posted member may be fabricated of a material which elastically deforms, and thereby fixedly secures the stabilization member when the locking device is threadably advanced into the coupling mechanism. By way of example, the posted member could be formed from a deformable plastic material, such as polyetheretherkeytone (PEEK) polymer. Alternatively, the posted member could be fabricated from another deformable material comprising carbon fiber composite polymers, UHMWPE, shape memory metals, resorable polymers, bio-inert polymeric materials, thermoplastic polymers, thermoset polymers, or any combination of these materials. Still further, the posted member could be fabricated from a biocompatible metal or metal alloy.

Figure 11A:
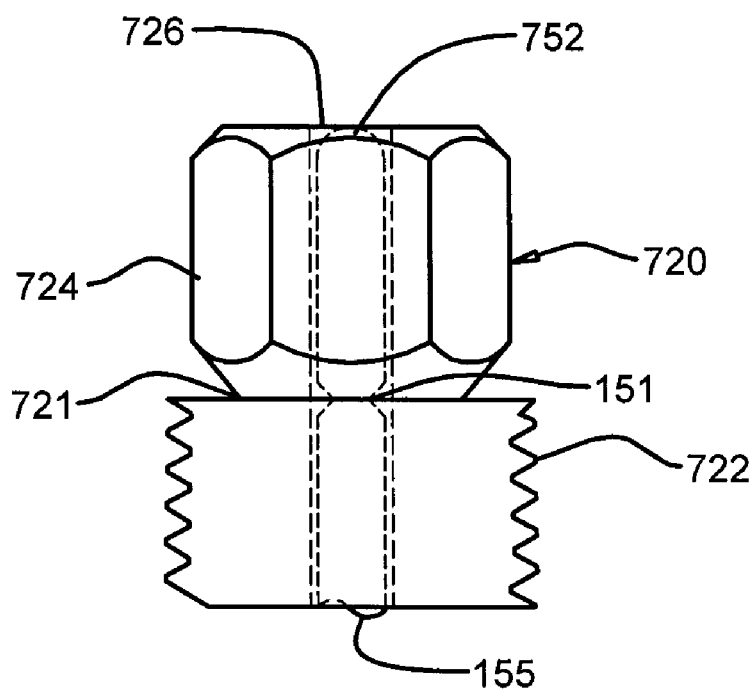
FIG. 11A is an elevational view of an alternate embodiment of a seating member, with a partial post of a posted member disposed therein, in accordance with an aspect of the present invention.

FIG. 11A depicts an alternate embodiment of a seating member 720, and a partial post 155 extending into a center opening 726 provided therein. In this embodiment, a break-off line 721 is defined circumferentially about seating member 720 between threaded portion 722 and drive tool receiving portion 724. Drive tool receiving portion 724 is again provided with a hexagonal-shaped perimeter to facilitate coupling of the drive tool to the seating member. Aligned with break-off line 721 is a break-off line 151 in post 155. With this embodiment, once the seating member is fully operationally engaged with the coupling mechanism to fixate the stabilization member, the drive tool (described below) is employed to break off both the drive tool receiving portion 724 of the seating member, and the break-off post portion of post 155 at the aligned break-off lines 721 & 151.

FIGS. 12A & 12B depict a further embodiment of a seating member for a locking device, in accordance with an aspect of the present invention. In this embodiment, seating member 820 includes a threaded portion 822 and a drive tool receiving portion 824. As shown, drive tool receiving portion 824 is configured with an internal hexagonal-shaped opening 828 extending therein. The hexagonal-shaped opening 828 in this example is aligned with the post receiving opening 826, and depending upon the implementation of the surgical drive tool, the post (not shown) of the posted member may extend into hexagonal-shaped opening 828, or even through opening 828, and thereby extend through the seating member into the drive tool when the surgical drive tool engages the seating member. (In this regard, see FIGS. 13 & 14.) FIG. 12B depicts a top plan view of seating member 820, wherein the hexagonal-shaped internal opening 828 is illustrated within the tool receiving upper portion 824 of the seating member.

FIG. 12C depicts a top plan view of an alternate embodiment of a drive tool receiving portion 834 of a seating member. In this embodiment, receiving portion 834 has an internal hexalobular-shaped opening 838 for engagement by a surgical drive tool (not shown). As in the embodiment of FIG. 12A, the post receiving opening (not shown) within the seating member may be aligned with internal hexalobular-shaped opening 838 to allow the post of the posted member to extend into, or even through, the drive tool receiving portion 834 of the seating member.

Figure 13:
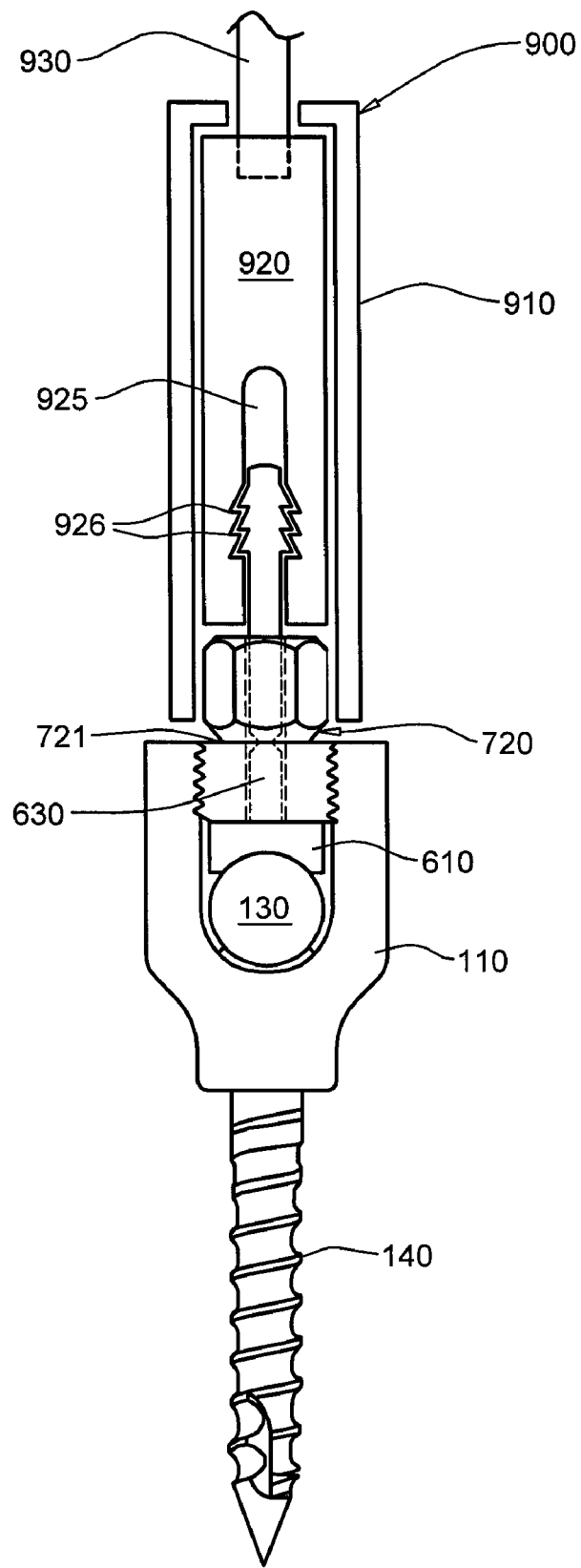
FIG. 13 is an elevational view of a bone stabilization system and surgical drive tool operatively engaging the locking device of the bone stabilization system, in accordance with an aspect of the present invention.

FIG. 13 depicts one embodiment of a surgical drive tool 900 (in accordance with an aspect of the present invention) shown operatively engaging a seating member 720 of a locking device, which is fully threadably coupled to a coupling mechanism 110 interfacing stabilization member 130 to a bone anchor 140. As shown, drive tool 900 includes a first component 910, such as a rotatable outer shaft, which is configured (in one embodiment) with a hexagonal-shaped opening sized to receive the drive tool receiving portion of seating member 720. A second component 920, for example, comprising an inner shaft, includes post receiving opening 925 with barb-receiving indents 926 in an inner wall thereof configured to receive a barbed post 630 of the posted member. In this example, the posted member is assumed to comprise a configuration similar to that described above in connection with FIG. 9B. The surgical drive tool 900 further includes a torque driver connection 930 which can be employed to selectively lock the first and second components 910 & 920 together so that the component 920 turn together. This feature of the surgical drive tool is employed to facilitate twist-off break-away of the drive tool receiving portion of seating member 720, as well as the break-away post portion of post 630, at the break-off line 721 of seating member 720 and the aligned break-off line of the post. For example, after threadably engaging seating member 720 fully into coupling mechanism 110, torque driver connection 930 may be employed to lock the first and second components 910 & 920 together, after which a sufficient torque is applied to twist off the drive tool receiving portion of seating member 720 along break-off line 721 and the break-off portion of post 630 at the aligned break-off line.

Figures 14, 14A:
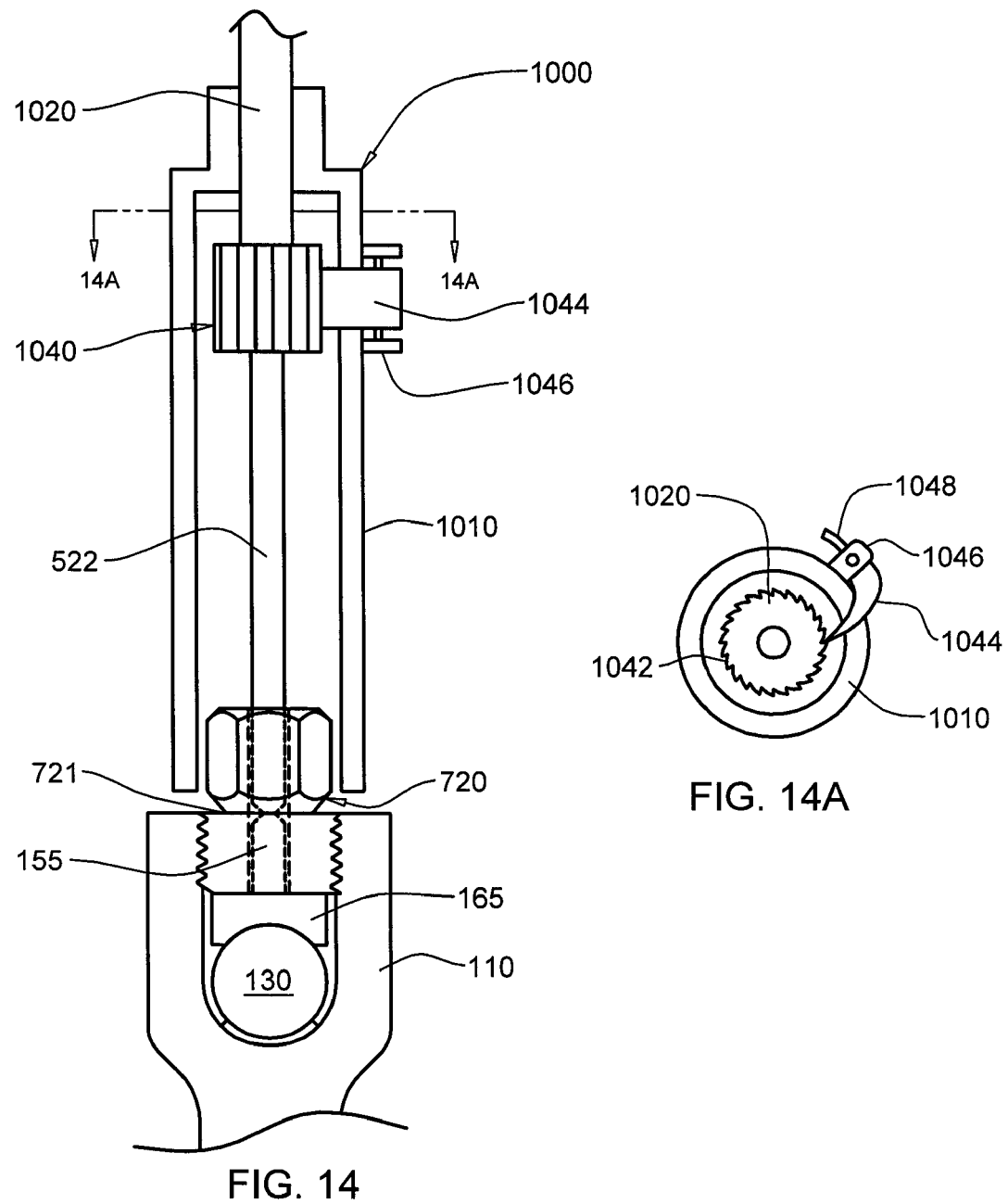
FIG. 14 is a partial elevational view of another embodiment of a bone stabilization device and surgical drive tool operatively engaging the locking device of the bone stabilization system, in accordance with an aspect of the present invention.
FIG. 14A is a cross-sectional elevational view of the surgical drive tool FIG. 14 taken along line 14-14, in accordance with an aspect of the present invention.

FIGS. 14 & 14A depict an alternate embodiment of a surgical drive tool 1000 (in accordance with an aspect of the present invention), shown operatively engaging a seating member 720 of a locking device, which is fully threadably coupled to a coupling mechanism 110 interfacing stabilization member 130 to a bone anchor (not shown). Drive tool 1000 includes a first component 1010, such as a rotatable outer shaft, configured with a hexagonal-shaped internal opening sized to receive the drive tool receiving portion of seating member 720, and a second component 1020, such as an inner shaft configured with an opening sized to receive a break-off portion 522 of a post 155 of the posted member.

In this embodiment, the first and second components are interconnected by a gear and pawl mechanism 1040. As shown in the cross-sectional view of FIG. 14A, the gear and pawl mechanism 1040 includes a gear 1042 affixed to second component 1020 and a pawl 1044 mounted via a bracket 1046 to first component 1010. The gear and pawl mechanism 1040 is configured to allow first component 1010 to freely rotate in one direction to facilitate threadable engagement of the seating member 720 with coupling mechanism 110. Once fully engaged, a sufficient torque is applied to the first component to break off the drive tool receiving portion of seating member 720 along break-off line 721. By turning the first component 1010 in an opposite direction, the gear and pawl mechanism 1040 locks, allowing the application of a sufficient torque to then twist off the break-off portion 522 of post 155. As shown, pawl 1044, which is either external or internal the first component, is provided with a handle 1048 to allow for release of the pawl from the gear.

Figure 15:
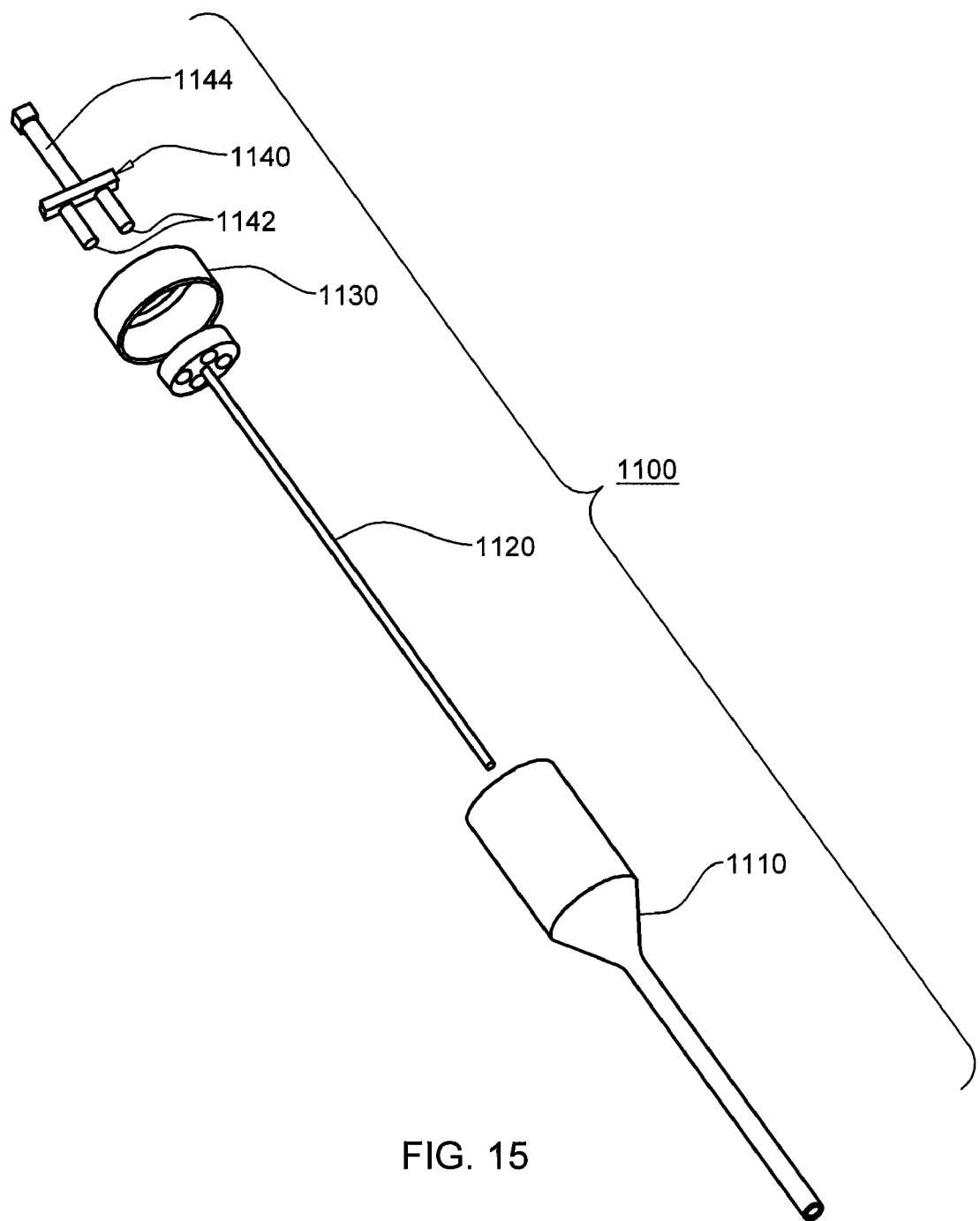
FIG. 15 is an exploded view of an alternate embodiment of a surgical drive tool for engaging a locking device of a bone stabilization system, in accordance with an aspect of the present invention.
Figure 15A:
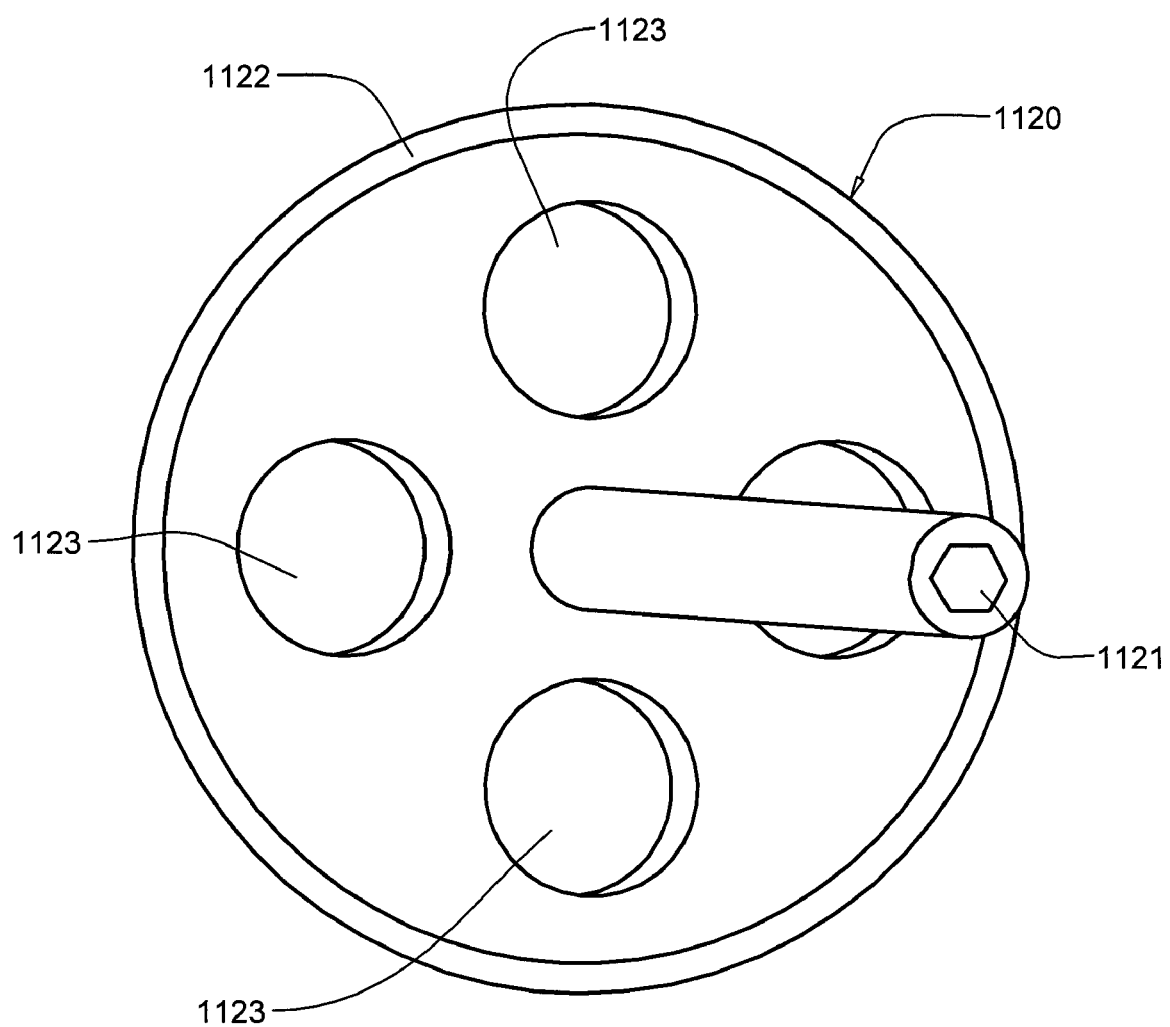
FIG. 15A is an isometric view of the inner shaft component of the surgical drive tool of FIG. 15, in accordance with an aspect of the present invention.

FIG. 15 depicts another embodiment of a surgical drive tool 1100, in accordance with an aspect of the present invention. This surgical drive tool is similar to the tool embodiment of FIG. 13, with the torque drive connection being shown in greater detail in FIG. 15. As shown, a first component 1110, such as a rotatable outer shaft, has an opening in one end sized to engage a drive tool receiving portion of a seating member (not shown). The surgical drive tool 1100 further includes a second component 1120, comprising an inner shaft having an opening sized to receive a portion of the post of the posted member (not shown). A disc 1122 resides at the proximal end of second component 1120 and includes multiple openings 1123 therein (see FIG. 15A). The end opening 1121 in second component 1120, which is shown to be hexagonal-shaped in FIG. 15A, is sized and configured to receive a hexagonal-shaped posted member such as illustrated above in connection with FIGS. 10B & 10C (by way of example). The surgical drive tool further includes a cap 1130 affixed to first component 1110, and within which disc 1122 resides, and a torque driver connection 1140, which in this embodiment comprises a plate having a drive post 1144 and two members 1142 extending from opposite surfaces thereof. When the surgical drive tool 1100 is in use, the torque driver connection 1140 is selectively employed to lock movement of second component 1120 relative to first component 1110, in a manner similar to that described above in connection with FIG. 13. This is achieved by placing members 1142 of the torque drive connection 1140 through appropriately aligned openings in cap 1130 (not shown) and openings 1123 in disc 1122. By way of example, the proximal end of drive arm 1144 is square-shaped to mate to a square-shaped driver (not shown), rotation of which would cause the first and second component to rotate together.

In view of the above description, those skilled in the art will note that a method for stabilizing a spinal column is presented herein. This method includes: providing a bone stabilization system comprising a bone anchor, a stabilization member, a coupling mechanism, and a locking device, wherein the coupling mechanism is configured to couple the stabilization member to the bone anchor, and the locking device is operatively associated with the coupling mechanism, and wherein the locking device further includes a seating member configured to threadably engage the coupling mechanism and a posted member configured to control the stabilization member as the seating member threadably engages the coupling mechanism, the posted member comprising an interface member and at least one post extending therefrom, and wherein the seating member includes at least one opening therein; positioning the stabilization member in the coupling mechanism; positioning the posted member with the at least one post thereof within the at least one opening of the seating member, and threading the seating member into the coupling mechanism while holding the at least one post of the posted member fixed and in physical contact with the stabilization member, thereby maintaining control of the stabilization member as the seating member engages the coupling mechanism; and continuing to threadably advance the seating member into the coupling mechanism, thereby causing the posted member to become fixed between the seating member and the stabilization member, and securing the stabilization member between the posted member and the coupling mechanism.

In further aspects, the method includes employing a surgical drive tool for performing the threading of the seating member into the coupling mechanism and the holding of the at least one post of the posted member fixed and in physical contact with the stabilization member. The surgical drive tool includes a first component configured to operatively engage the seating member to facilitate the threading of the seating member into the coupling mechanism and a second component configured to operatively engage the at least one post of the posted member to facilitate holding of the at least one post of the posted member fixed and in physical contact with the stabilization member.

The method can further include breaking off at least one of a portion of the seating member after threadable engagement of the seating member within the coupling mechanism, or a portion of at least one post of the posted member. Providing of the seating member can include providing a circumferential break-off line extending around the perimeter thereof, and continuing to advance the seating member can include continuing to advance the seating member within the coupling mechanism until break off of a break-off portion of the seating member along the circumferential break-off line thereof is achieved. Further, the providing can include providing the at least one post of the posted member with a circumferential break-off line extending around the perimeter thereof, and the method can further include breaking off a portion of the at least one post after threadably advancing the seating member into the coupling mechanism, and causing the posted member to become fixedly positioned between the seating member and the stabilization member.

To summarize, those skilled in the art will note from the above description that provided herein is an enhanced locking device for a bone stabilization system, as well as surgical drive tools for inserting/extracting the locking device and surgical methods for stabilizing a column employing a bone stabilization system and the enhanced locking device. The bone stabilization system includes a bone anchor, a coupling mechanism, and a stabilization member, wherein the coupling mechanism is configured to couple the stabilization member to the bone anchor. The enhanced locking device includes a seating member and a posted member. The seating member is operatively associated with the coupling mechanism for securing a stabilization member within the coupling mechanism, and includes at least one opening therein. The posted member includes an interface member and at least one post extending therefrom. The posted member is configured for disposition between the seating member and the stabilization member with the at least one post extending from the interface member being received into the at least one opening of the seating member when the seating member is employed to secure the stabilization member within the coupling mechanism.

Advantageously, the at least one post is sized to facilitate handling of the separate seating member and posted member pieces, as well as to control the stabilization member as the seating member operatively engages the coupling mechanism to secure the stabilization member within the coupling mechanism with the posted member disposed between the seating member and the stabilization member. Numerous variations on the seating member and posted member designs, as well as various embodiments of the surgical drive tool, are depicted and described herein.

By way of example, the distal surface of the interface member of the posted member can comprise a number of different geometries, including planar and saddle-style contoured. A saddle-style contoured geometry that follows the outer periphery of the stabilization member is beneficial for semi-rigid stabilization members because the surface allows the force on the stabilization member to be distributed across the entire geometry. Those skilled in the art will note, however, that the geometric shape of the distal interface surface of the posted member is not limited to the surfaces described herein. Further, the outer profile of the interface member is not constrained to being enclosed by the perimeter of the coupling mechanism. That is, the interface member may extend past the through slots in the coupling mechanism.

The one or more posts of the posted member can be located along the central axis of the interface member, or offset therefrom. Based on load distribution of the locking device to the stabilization member, it may be desirable to offset the one or more posts from the central axis of the interface member. Typically, the direction the posts could shift would either be cranial or caudal, based on how the bone anchor is situated. However, the post is not limited to these orientations. By offsetting the post from the center axis of the interface member, load may be distributed along the interface member, but allow for variable load characteristics to be present, for example, to maintain a semi-rigid stabilization member in a desired manner.

The surgical drive tool presented herein is designed to grip the outer geometry of the one or more posts of the posted member, as well as to grip the drive tool receiving portion of the seating member, either externally or internally. The surgical drive tool may have a barb-style or cam-style inner shaft that would grip the outer geometry of the post, locking it in place the further the post is inserted into the surgical drive tool. In addition, the surgical drive tool could have a one-way clutch that would allow rotation of the drive tool in a direction for tightening of the seating member into the coupling mechanism, and if the drive tool is rotated in the opposite direction from the "driving" direction, then the instrument tightens on the post to separate at least a portion of the post from the posted member. The surgical drive tool may also have an internal shaft with geometry such that it would grip the upper most portion of the post, i.e., a hexagonal-style or a hexalobular-shaped geometry.

In use, the upper portion of the seating member is inserted and retained within the surgical drive tool, after which the posted member is inserted through the seating member into the surgical drive tool. The drive tool grips the one or more posts via the external geometry of the posts and allows the seating member of the locking device to be held in place between the posted member and the surgical drive tool. Once the locking device has been seated into the coupling mechanism, the post is then separated and removed, or the height of the post is reduced by twist-off so that the remaining post height does not extend an unacceptable level past the seating member. Removal of the post could be performed by a number of methods, including cutting of the post, or employing a twist off technique such as described above.

Although the preferred embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A locking device for use in a bone stabilization system, the bone stabilization system including a bone anchor, a coupling mechanism and a stabilization member, wherein the coupling mechanism is configured to couple the stabilization member to the bone anchor, the locking device comprising:
    a seating member having a height H and operatively associated with the coupling mechanism for securing the stabilization member within the coupling mechanism, the seating member being configured with at least one opening therein;
    a posted member comprising an interface member and at least one post extending therefrom a distance D, the posted member being configured for disposition between the seating member and the stabilization member with the at least one post extending from the interface member being received into at least one opening of the seating member when the seating member is employed to secure the stabilization member within the coupling mechanism; and
    wherein the distance D of the at least one post is at least equal to the height H of the seating member to facilitate control of the stabilization member as the seating member operatively engages the coupling mechanism to secure the stabilization member within the coupling mechanism with the posted member disposed between the seating member and the stabilization member.

2. The locking device of claim 1, wherein the at least one post extending distance D allows a surgical drive tool to couple thereto and to hold the at least one post fixed and in physical contact with the stabilization member, thereby facilitating control of the stabilization member as the seating member operatively engages the coupling mechanism.

3. The locking device of claim 1, wherein the at least one post is a central post, and wherein the at least one opening in the seating member comprises a central opening extending axially therethrough.

4. The locking device of claim 1, wherein the interface member includes a proximal surface and a distal surface, the at least one post extending from the proximal surface, and the distal surface interfacing with the stabilization member when the posted member is disposed in operative position between the seating member and the stabilization member.

5. The locking device of claim 4, wherein the distal surface comprises one of a planar surface or a contoured surface, the contoured surface being contoured to mate to an exterior portion of the stabilization member when the posted member is disposed in operative position between the seating member and the stabilization member.

6. The locking device of claim 5, wherein the distal surface further comprises at least one protrusion extending therefrom configured to facilitate maintenance of the stabilization member in fixed position within the coupling mechanism between the coupling mechanism and the posted member when the posted member is disposed in operative position between the seating member and the stabilization member.

7. The locking device of claim 1, wherein the at least one post comprises an elongate central post having a transverse cross-section comprising one of a circular cross-section, a triangular cross-section, a rectangular cross-section, or a hexagonal cross-section.

8. The locking device of claim 7, wherein the seating member comprises a threaded portion and a surgical tool receiving portion, the surgical tool receiving portion comprising one of an outer hexagonal-shaped perimeter, an internal hexagonal-shaped opening or an internal hexalobular-shaped opening.

9. The locking device of claim 1, wherein the seating member comprises a threaded portion and a surgical tool receiving portion, and wherein the seating member further comprises a circumferential break-off line extending around the perimeter thereof between the threaded portion and the surgical tool receiving portion, the circumferential break-off line facilitating removal of the surgical tool receiving portion after the seating member is employed to secure the stabilization member within the coupling mechanism.

10. The locking device of claim 1, wherein the at least one post further comprises at least one gripping barb extending therefrom or at least one key slot formed therein to facilitate capture of the at least one post by a surgical drive tool employed to secure the seating member in operative position relative to the coupling mechanism and thereby secure the stabilization member within the coupling mechanism.

11. A locking device for use in a bone stabilization system, the bone stabilization system including a bone anchor, a coupling mechanism and a stabilization member, wherein the coupling mechanism is configured to couple the stabilization member to the bone anchor, the locking device comprising:
    a seating member operatively associated with the coupling mechanism for securing the stabilization member within the coupling mechanism, the seating member being configured with at least one opening therein;
    a posted member comprising an interface member and at least one post extending therefrom, the posted member being configured for disposition between the seating member and the stabilization member with the at least one post extending from the interface member being received into at least one opening of the seating member when the seating member is employed to secure the stabilization member within the coupling mechanism; and
    wherein the at least one post is sized to facilitate control of the stabilization member as the seating member operatively engages the coupling mechanism to secure the stabilization member within the coupling mechanism with the posted member disposed between the seating member and the stabilization member,
    wherein the at least one post comprises a post having a break-off post portion which is removed after the seating member is employed to secure the stabilization member within the coupling mechanism.

12. The locking device of claim 11, wherein the break-off post portion is defined by a circumferential break-off line extending around the perimeter of the post.

13. The locking device of claim 12, wherein the circumferential break-off line is at a junction between the post and a proximal surface of the interface member.

14. The locking device of claim 12, wherein the post is an elongate post having a first end and a second end, and wherein the circumferential break-off line is disposed intermediate the first end and second end of the post.

15. The locking device of claim 12, wherein the circumferential break-off line is disposed within the seating member when post is received within the at least one opening of the seating member and the seating member is employed to secure the stabilization member within the coupling mechanism, wherein once the break-off post portion is removed, a remaining post portion extends within the seating member a distance less than or equal to the height H of the seating member.

16. The locking device of claim 15, wherein the seating member further comprises a circumferential break-off line extending around the perimeter thereof, and wherein the seating member comprises a break-off portion which is removed after the seating member is employed to secure the stabilization member within the coupling mechanism.

17. The locking device of claim 16, wherein the circumferential break-off line of the post is aligned with the circumferential break-off line of the seating member when the posted member is disposed in operational position with the post extending into the at least one opening of the seating member.

18. A bone stabilization system comprising:
a bone anchor;
a stabilization member;
a coupling mechanism, wherein the coupling mechanism is configured to operatively connect the bone anchor and the stabilization member; and
a locking device, wherein the locking device operatively connects to the coupling mechanism to secure the stabilization member within the coupling mechanism, and wherein the locking device comprises:
a seating member having a height H and operatively associated with the coupling mechanism for securing the stabilization member within the coupling mechanism, the seating member being configured with at least one opening therein;
a posted member comprising an interface member and at least one post extending therefrom a distance D, the posted member being configured for disposition between the seating member and the stabilization member with the at least one post extending from the interface member being received into the at least one opening of the seating member when the seating member is employed to secure the stabilization member within the coupling mechanism; and
wherein the distance D of the at least one post is at least equal to the height H of the seating member to facilitate control of the stabilization member as the seating member operatively engages the coupling mechanism to secure the stabilization member within the coupling mechanism with the posted member disposed between the seating member and the stabilization member.

19. The bone stabilization system of claim 18, wherein the at least one post extending distance D allows a surgical drive tool to couple thereto to hold the posted member fixed and in physical contact with the stabilization member, thereby facilitating control of the stabilization member as the seating member operatively engages the coupling mechanism.

20. The bone stabilization system of claim 19, wherein the seating member threadably engages the coupling mechanism for securing the stabilization member within the coupling mechanism, and wherein the distance D allows the surgical drive tool to hold the posted member fixed while threading the seating member into the coupling mechanism, wherein threading of the seating member into the coupling mechanism results in applying a load to the interface member of the posted member, thereby securing the stabilization member between the posted member and the coupling mechanism.

21. The bone stabilization system of claim 18, wherein the at least one post extending from the interface member the distance D is a central post extending from the interface member, and wherein the at least one opening in the seating member comprises a central opening extending axially therethrough.

22. The bone stabilization system of claim 18, wherein the interface member includes a proximal surface and a distal surface, the at least one post extending from the proximal surface and the distal surface interfacing with the stabilization member when the posted member is disposed in operative position between the seating member and the stabilization member, the distal surface comprising one of a planar surface or a contoured surface, the contoured surface being contoured to mate to an exterior portion of the stabilization member when the posted member is disposed in operative position between the seating member and the stabilization member.

23. The bone stabilization system of claim 22, wherein the distal surface further comprises at least one protrusion extending therefrom configured to facilitate maintenance of the stabilization member in fixed position within the coupling mechanism between the coupling mechanism and the posted member when the posted member is disposed in operative position between the seating member and the stabilization member.

24. The bone stabilization system of claim 18, wherein the at least one post comprises an elongate post having a transverse cross section comprising one of a circular cross-section, a triangular cross-section, a rectangular cross-section, or a hexagonal cross-section.

25. The bone stabilization system of claim 24, wherein the at least one post further comprises at least one gripping barb extending therefrom or at least one key slot formed therein to facilitate capture of the at least one post by a surgical drive tool employed to secure the seating member in operative position relative to the coupling mechanism and thereby secure the stabilization member within the coupling mechanism.

26. The bone stabilization system of claim 18, wherein the stabilization member is an elongate orthopaedic implant having a first end and a second end and a longitudinal axis extending therebetween, wherein when the locking device is in use, the stabilization member is received within the coupling mechanism and the posted member of the locking device engages the stabilization member along the longitudinal axis thereof.

27. A bone stabilization system comprising:
a bone anchor;
a stabilization member;
a coupling mechanism, wherein the coupling mechanism is configured to operatively connect the bone anchor and the stabilization member; and a locking device, wherein the locking device operatively connects to the coupling mechanism to secure the stabilization member within the coupling mechanism, and wherein the locking device comprises:
- a seating member operatively associated with the coupling mechanism for securing the stabilization member within the coupling mechanism, the seating member being configured with at least one opening therein;
- a posted member comprising an interface member and at least one post extending therefrom, the posted member being configured for disposition between the seating member and the stabilization member with the at least one post extending from the interface member being received into the at least one opening of the seating member when the seating member is employed to secure the stabilization member within the coupling mechanism; and
- wherein the at least one post is sized to facilitate control of the stabilization member as the seating member operatively engages the coupling mechanism to secure the stabilization member within the coupling mechanism with the posted member disposed between the seating member and the stabilization member, wherein the at least one post comprises a post having a break-off post portion which is removed after the seating member is employed to secure the stabilization member within the coupling mechanism.

28. The bone stabilization system of claim 27, wherein the post is an elongate post having a first end and a second end, and wherein the break-off post portion is defined by a circumferential break-off line disposed intermediate the first and second end of the post.

29. The bone stabilization system of claim 27, wherein the break-off post portion of the post is defined by a circumferential break-off line extending around the perimeter of the post, and wherein the circumferential break-off line is disposed within the seating member when the post is received within the at least one opening of the seating member and the seating member is employed to secure the stabilization member within the coupling mechanism, and wherein once the break-off post portion is removed, a remaining post portion extends within the seating member a distance less than or equal to a height H of the seating member.

30. The bone stabilization system of claim 29, wherein the seating member further comprises a circumferential break-off line extending around the perimeter thereof, and wherein the seating member comprises a break-off portion which is removed after the seating member is employed to secure the stabilization member within the coupling mechanism.

31. The bone stabilization system of claim 30, wherein the circumferential break-off line of the post is aligned with the circumferential break-off line of the seating member when the posted member is disposed in operational position with the post extending into the at least one opening of the seating member.

* * * * *